US010195647B2

(12) United States Patent
Justice et al.

(10) Patent No.: US 10,195,647 B2
(45) Date of Patent: Feb. 5, 2019

(54) METHOD AND APPARATUS FOR SORTING

(71) Applicants: Timothy L. Justice, Walla Walla, WA (US); Johan Calcoen, Leuven (BE); Dirk Adams, Tongeren (BE); Gerald R. Richert, Walla Walla, WA (US)

(72) Inventors: Timothy L. Justice, Walla Walla, WA (US); Johan Calcoen, Leuven (BE); Dirk Adams, Tongeren (BE); Gerald R. Richert, Walla Walla, WA (US)

(73) Assignee: Key Technology, Inc, Walla Walla, WA (US)

( * ) Notice: Subject to any disclaimer, the term of this patent is extended or adjusted under 35 U.S.C. 154(b) by 0 days.

(21) Appl. No.: 15/708,743

(22) Filed: Sep. 19, 2017

(65) Prior Publication Data
US 2018/0029085 A1    Feb. 1, 2018

Related U.S. Application Data

(63) Continuation-in-part of application No. 14/997,173, filed on Jan. 15, 2016, now Pat. No. 9,795,996.

(51) Int. Cl.
*B07C 5/34* (2006.01)
*B07C 5/342* (2006.01)
*G01N 21/85* (2006.01)
*G01N 21/88* (2006.01)
*G01N 21/89* (2006.01)

(52) U.S. Cl.
CPC .............. *B07C 5/342* (2013.01); *B07C 5/34* (2013.01); *B07C 5/3422* (2013.01); *B07C 5/3425* (2013.01); *G01N 21/8806* (2013.01); *G01N 21/89* (2013.01); *B07C 2501/0018* (2013.01); *B07C 2501/0081* (2013.01); *G01N 21/85* (2013.01); *G01N 2201/062* (2013.01); *G01N 2201/0636* (2013.01); *G01N 2201/06113* (2013.01); *G01N 2201/06193* (2013.01)

(58) Field of Classification Search
CPC ...... B07C 5/342; B07C 5/3416; G01N 21/85; G01N 21/89; G01N 21/8806; G01N 2201/062; G01N 2201/06113
USPC .......................... 209/552, 576, 577, 587, 588
See application file for complete search history.

(56) References Cited

U.S. PATENT DOCUMENTS

| 4,154,672 A * | 5/1979 | Wiley .................... B07C 5/3416 378/89 |
| 4,369,886 A | 1/1983 | Lane et al. |
| 4,834,870 A | 5/1989 | Osterberg et al. |

(Continued)

FOREIGN PATENT DOCUMENTS

| EP | 1083007 A2 | 3/2001 |
| EP | 3210677 A1 | 8/2017 |

OTHER PUBLICATIONS

PCT International Search Report dated Aug. 17, 2015.
(Continued)

*Primary Examiner* — Terrell H Matthews
(74) *Attorney, Agent, or Firm* — Randall Danskin P.S.

(57) ABSTRACT

A method and apparatus for sorting objects is described, and which provides high-speed image data acquisition to fuse multiple data streams in real-time, while avoiding destructive interference when individual sensors or detectors are utilized in providing data regarding internal and external features and characteristics and qualities of products being inspected.

16 Claims, 11 Drawing Sheets

(56) References Cited

U.S. PATENT DOCUMENTS

| | | | |
|---|---|---|---|
| 5,260,576 A * | 11/1993 | Sommer, Jr. | B07C 5/3416 |
| | | | 209/522 |
| 5,471,311 A | 11/1995 | van den Bergh et al. | |
| 5,659,624 A | 8/1997 | Fazzari et al. | |
| 5,675,419 A | 10/1997 | van den Bergh et al. | |
| 5,761,070 A | 6/1998 | Conners et al. | |
| 5,954,206 A | 9/1999 | Mallon et al. | |
| 6,016,194 A | 1/2000 | Girvin et al. | |
| RE36,537 E * | 2/2000 | Sommer, Jr. | B07C 5/3416 |
| | | | 209/576 |
| 6,060,677 A * | 5/2000 | Ulrichsen | B07C 5/342 |
| | | | 209/577 |
| 6,506,991 B1 * | 1/2003 | Eixelberger | B07C 5/3422 |
| | | | 209/581 |
| 6,734,383 B1 | 5/2004 | Calcoen et al. | |
| 6,914,678 B1 * | 7/2005 | Ulrichsen | B07C 5/342 |
| | | | 356/429 |
| 7,262,380 B1 * | 8/2007 | Ulrichsen | B07C 5/342 |
| | | | 209/577 |
| 7,292,949 B2 | 11/2007 | Ding | |
| 7,326,871 B2 | 2/2008 | Kenny et al. | |
| 7,541,557 B2 | 6/2009 | Voloshyn et al. | |
| 8,030,589 B2 * | 10/2011 | Huber | B07C 5/3416 |
| | | | 209/522 |
| 8,083,066 B2 | 12/2011 | Bourely | |
| 8,253,054 B2 | 8/2012 | Koehler et al. | |
| 8,283,589 B2 | 10/2012 | Janssens et al. | |
| 8,794,447 B2 | 8/2014 | Van Kasteren | |
| 8,902,416 B2 | 12/2014 | Klokkerud et al. | |
| 2003/0034281 A1 * | 2/2003 | Kumar | B07C 5/3425 |
| | | | 209/579 |
| 2003/0127366 A1 * | 7/2003 | Ikeda | B03C 1/14 |
| | | | 209/1 |
| 2007/0147585 A1 * | 6/2007 | Eilbert | G01N 23/04 |
| | | | 378/57 |
| 2012/0138514 A1 * | 6/2012 | Janssens | B07C 5/342 |
| | | | 209/577 |
| 2014/0054204 A1 * | 2/2014 | Christel | B07C 5/3425 |
| | | | 209/587 |
| 2014/0061103 A1 | 3/2014 | Ito et al. | |
| 2016/0252461 A1 | 9/2016 | Balthasar et al. | |
| 2018/0029085 A1 * | 2/2018 | Justice | B07C 5/34 |
| 2018/0056334 A1 * | 3/2018 | Justice | B07C 5/34 |

OTHER PUBLICATIONS

European Search Report, Application No. 115811496.7, dated Nov. 17, 2017.

L. Smeesters, Internal scattering as an optical screening method to identify peeled potatoes giving rise to an excess of acrylamide, Journal of Food Engineering, Mar. 10, 2016, pp. 255-261, vol. 195, Elsevier, Brussel, Belgium.

* cited by examiner

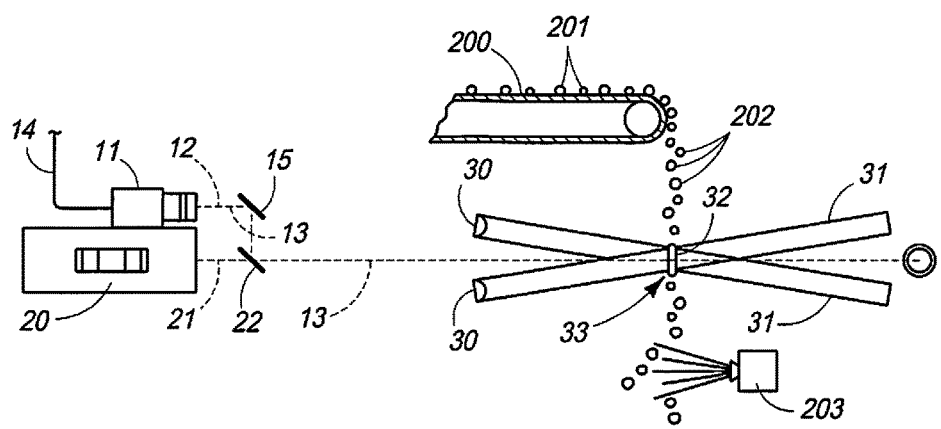
FIG. 1E
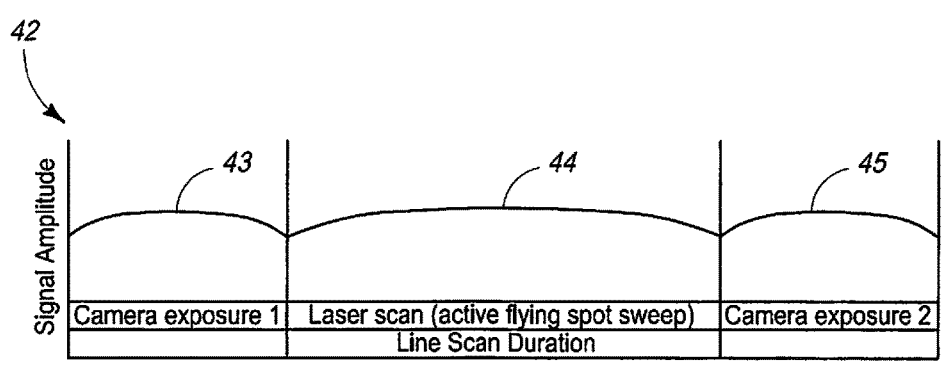
FIG. 1E1

METHOD AND APPARATUS FOR SORTING

TECHNICAL FIELD

The present invention relates to a method and apparatus for sorting, and more specifically to a method and apparatus for sorting a stream of products, and wherein the method and apparatus generates multi-modal, multi-spectral images which contain a multiplicity of simultaneous channels of data which contain information on color, polarization, fluorescence, texture, translucence, transmittance and other information which represents and/or is an indicator for various external and internal aspects or characteristics of an item being inspected and which further can be used for identification, and feature and flaw detection and for sorting.

BACKGROUND OF THE INVENTION

The present invention relates to a method and apparatus for sorting, and more specifically to a method for determining a defect in an agricultural product which typically cannot be visually discerned, and then removing the product having the agricultural defect or removing the defect itself, from a moving product stream.

It has long be known that camera images including, line scan cameras are commonly combined with laser scanners or LIDAR and/or time of flight imaging for three dimensional imaging and inspection, and which are used to perceive depth, and distance, and to further track moving objects, and the like. Such devices have been employed in sorting apparatuses of various designs in order to identify acceptable and unacceptable objects, or products, within a stream of products to be sorted, thus allowing the sorting apparatus to remove undesirable objects or products from the stream of products in order to produce a homogeneous product stream which is more useful for food processors, and the like. Heretofore, attempts which have been made to enhance the ability to inspect objects effectively, in real-time, have met with somewhat limited success. In the present application, the term "real-time" when used in this document, relates to information processing which occurs within the span of, and substantially at the same rate, as that which it is depicted. "Real-time" may include several microseconds to a few milliseconds.

One of the chief difficulties associated with such efforts has been that when particular emitters, illuminators, detectors, sensors, and the like have been previously employed, and then energized both individually and, in combination with each other, they have undesirable affects and limitations including, but not limited to, lack of isolation of the signals of different modes, but similar optical spectrum; unwanted changes in the response per optical angle of incidence, and field angle; a severe loss of sensitivity or effective dynamic range of the sensor being employed, among many others. Thus, the use of multiple sensors or interrogating means for gathering and providing information regarding the objects being sorted, when actuated, simultaneously, often destructively interfere with each other and thus limit the ability to identify external and internal features or characteristics of an object which would be helpful in classifying the object being inspected into different grades or classifications, or as being either, on the one hand, an acceptable product or object, or on the other hand, an unacceptable product or object, which needs to be excluded/removed from the product stream.

The developers of optical sorting systems which are uniquely adapted for visually inspecting a mass-flow of a given food product have endeavored, through the years, to provide increasing levels of information which are useful in making well-informed sorting decisions to effect sorting operations in mass-flow food sorting devices. While the creation of, capturing and processing of product images employing prior art cameras and other optical devices, such as but not limited to laser scanners, have long been known, it has also been recognized that images of a product formed by visible spectrum electromagnetic radiation often will not provide enough information for an automated sorting machine to accurately identify all (and especially hidden, internal or below surface) defects, and which may subsequently be later identified or develop after further processing of the product. For example, one of the defects in agricultural products which have troubled food processors through the years has been the effective identification of "sugar end" defects in potato products, and more specifically potato products that are destined for processing into food items such as French Fries, potato chips and the like.

Another example of a defect in agricultural products that has troubled food processors through the years has been the detection and/or identification of internal defects, or defects occurring below an external surface in agricultural products, including but not limited to detection of precursors of cancer-causing acrylamide (which is generated in high temperature cooking such as frying) and detection of other internal/below surface characteristics that are indicative of unacceptable items. Such characteristics may include, but are not limited to, the presence of chlorophyll which may be a predictor of the presence of solanine; and the detection of reducing sugars such as, but not limited to fructose and glucose that can react with asparagine to form acrylamide.

Chlorophyll, which is well known as causing the "green color" of plants frequently develops below the peel in potatoes that are exposed to light after harvesting. In small amounts, chlorophyll is not visually perceptible as "green" but the chlorophyll is nevertheless present and can cause the potato/piece of potato to be an unacceptable product. Further still, the presence of chlorophyll has been found to be a predictor of the presence of solanine and chaconine which are glyalkaloid poisons which have pesticide properties and which can cause illness if consumed. It is therefore important to identify potatoes and potato pieces having chlorophyll and to remove such potatoes and potato pieces from the product stream.

One of the primary methods to detect the presence of chlorophyll, which may be internal/below the surface, is through the detection and identification of chlorophyll fluorescence. Chlorophyll fluorescence occurs when chlorophyll is exposed to electromagnetic radiation which energizes the chlorophyll molecules which then emit light in the red and infra-red (IR) color spectrum. The irradiation of plant based food products with electromagnetic radiation, including but not limited to ultraviolet radiation and electromagnetic excitation, and the detection and identification of emitted electromagnetic radiation and/or fluorescent light provides a method for making a sorting decision based on non-visually perceptible characteristics of the items being sorted. Similarly, the identification of other hidden and/or internal and/or below surface characteristics that are precursors to harmful and/or unacceptable characteristics may similarly be identified or determined by exposing the product stream to electromagnetic radiation of various wavelengths and substantially simultaneously monitoring and detecting emitted or reflected or refracted electromagnetic radiation which is indicative of the particular precursor and/or characteristic.

For example, potato strips or French Fries made from "sugar end" potatoes exhibit or display undesirable dark-brown areas on the product after the potato piece has been subjected to frying. This defect is typically caused by the higher concentration of reducing sugars found in the given darkened region of the potato. The process of frying the product results in caramelizing, which creates the undesirable dark brown region on the fried product. The challenge for food processors has been that the "sugar end" defects are typically invisible to traditional optical detection technology until after the potato product has been cooked. In view of this situation, potato strip and potato chip processors can be unaware they have "sugar end" problems with a given lot of potatoes they are processing until their downstream food service customers fry the potato strips and chips and then provide complaints.

Those skilled in the art have recognized that a variety of factors can encourage development of such undesirable characteristics. It has further been found that reducing sugars can develop in tubers during cold storage prior to processing and that such reducing sugars may be converted back into sucrose (not a reducing sugar) by environmental conditions such as, but not limited to, warming the tubers to room temperature prior to cooking. As such, some of these undesirable characteristics can be difficult to detect and identify.

While the various prior art devices and methodology which have been used, heretofore, have worked with various degree of success, assorted industries such as food processors, and the like, have searched for enhanced means for discriminating between products or objects traveling in a stream so as to produce ever better quality products, or resulting products having different grades, for subsequent supply to various market segments.

A method and apparatus for sorting which avoids the detriments associated with the various prior art teachings, and practices utilized, heretofore, is the subject matter of the present application.

SUMMARY OF THE INVENTION

A first aspect of the present invention relates to a method and apparatus for sorting which includes providing a source of a product to be sorted, the product comprised of a plurality of individual items each having a multitude of external and internal characteristics that are perceptible, and wherein the multitude of external and internal characteristics that are perceptible are selected from a group including color; light polarization; light fluorescence; light reflectance; light scatter; light transmittance; surface texture; translucence; density; composition; structure and constituents, and wherein the multitude of external and internal characteristics that are perceptible can be detected and identified at least in part, from electromagnetic radiation which is spectrally reflected, refracted, fluoresced absorbed or transmitted by the multitude of external and internal perceptible characteristics of each of the plurality of individual items; conveying the plurality of individual items along a path of travel, and then releasing the plurality of individual items into a product stream for unsupported movement through a downstream inspection station for selective irradiation and contemporaneous collection of electromagnetic radiation which is either transmitted, reflected, refracted, fluoresced, emitted and/or scattered from each of the plurality of individual items; selectively energizing a first electromagnetic radiation emitter which is positioned on a first side of the product stream, and which, when energized, emits electromagnetic radiation at a first side of each of the plurality of individual items traveling in the unsupported product stream which is moving through the inspection station; selectively actuating a first electromagnetic radiation capturing device which is operably associated with the first electromagnetic radiation emitter, and which is further positioned on the first side of the unsupported product stream, and which, when actuated, captures electromagnetic radiation which is transmitted, reflected, refracted, fluoresced, emitted or scattered from each of the plurality of individual items and which are subjected to the electromagnetic radiation which was emitted by the energized first electromagnetic radiation emitter, and wherein the selectively actuated first electromagnetic radiation capturing device further generates a first interrogation signal; selectively energizing a second electromagnetic radiation emitter which is positioned on the first side of the unsupported product stream, and which, when energized, emits a narrow beam of electromagnetic radiation which is scanned along a path of travel, and across the unsupported product stream moving through the inspection station; selectively actuating a second electromagnetic radiation capturing device which is operably associated with the second electromagnetic radiation emitter, and which is further positioned on the first side of the product stream, and which, when actuated, captures electromagnetic radiation which is transmitted, reflected, refracted, fluoresced, emitted or scattered from each of the plurality of individual items moving through the inspection station, and which are subjected to the narrow beam of electromagnetic radiation emitted by the selectively energized second electromagnetic radiation emitter, and wherein the selectively actuated second electromagnetic radiation capturing device further generates a second interrogation signal; selectively energizing a third electromagnetic radiation emitter which is positioned on a second side of the unsupported product stream, and which, when energized, emits electromagnetic radiation which is directed at a second side of each of the plurality of individual items traveling in the unsupported product stream which is moving through the inspection station; selectively actuating a third electromagnetic radiation capturing device which is operably associated with the third electromagnetic radiation emitter, and which is further positioned on the second side of the product stream, and which, when actuated, captures electromagnetic radiation which is transmitted, reflected, refracted, fluoresced, emitted or scattered from each of the plurality of individual items moving through the inspection station, and which are subjected to the electromagnetic radiation emitted by the selectively energized third electromagnetic radiation emitter, and wherein the selectively actuated third electromagnetic radiation capturing device further generates a third interrogation signal; selectively energizing a fourth electromagnetic radiation emitter which is positioned on the second side of the unsupported product stream, and which, when energized, emits a narrow beam of electromagnetic radiation which is scanned along a path of travel, and across the unsupported product stream moving through the inspection station; selectively actuating a fourth electromagnetic radiation capturing device which is operably associated with the fourth electromagnetic radiation emitter, and which is further positioned on the second side of the product stream, and which, when actuated, captures electromagnetic radiation which is transmitted, reflected, refracted, fluoresced, emitted or scattered from each of the plurality of individual items moving through the inspection station, and which are subjected to electromagnetic radiation by the narrow beam of electromagnetic radiation emitted by the selectively energized fourth electromagnetic radiation emitter, and wherein the fourth selectively actuated electromagnetic radiation capturing device further generates a fourth interrogation signal; controllably coupling a controller with the first, second, third, and fourth selectively energizable electromagnetic radiation emitters, and each of the selectively actuated electromagnetic radiation capturing devices, respectively, and wherein the controller selectively and individually energizes the respective first, second, third, and fourth electromagnetic radiation emitters, and selectively and individually actuates each of the electromagnetic radiation capturing devices, in a predetermined sequence, so that only a predetermined electromagnetic radiation emitter and associated electromagnetic radiation capturing device or a cooperating combination of electromagnetic radiation emitters, and associated electromagnetic radiation capturing devices are selectively actuated or rendered operable, during a predetermined time period so as to substantially isolate the interrogation signals derived from each of the selectively actuated electromagnetic radiation capturing devices and to substantially impede spectral overlap, so as to prevent a destructive interference from developing between the respective selectively energized electromagnetic radiation emitters, and selectively actuated electromagnetic radiation capturing devices, and wherein the controller further receives the respective interrogation signals generated by the respective first, second, third, and fourth selectively actuated electromagnetic radiation capturing devices; analyzing with the controller, the respective interrogation signals received from the respective first, second, third, and fourth electromagnetic radiation capturing devices and detecting the multitude of external and internal characteristics of each of the plurality of individual items that are perceptible, and identifying individual items in the unsupported product stream that are acceptable and unacceptable, and wherein the controller generates, a product ejection signal when an unacceptable item is identified; and providing a product ejector downstream of the inspection station, and which receives the product ejection signal, and which ejects any of the plurality of individual items moving along the unsupported path of travel in the product stream that have been identified by the controller as unacceptable.

Still another aspect of the present invention relates to a method and apparatus for sorting which includes aligning the respective first and second selectively energizable electromagnetic radiation emitters, and associated selectively actuated electromagnetic radiation capturing devices with each other to focus on a single focal plane, and locating the third and fourth selectively energizable electromagnetic radiation emitters, and associated selectively actuated electromagnetic radiation capturing devices, on the opposite side of the unsupported product stream and orienting the third and fourth selectively energizable electromagnetic radiation emitters and associated selectively actuated electromagnetic radiation capturing devices to focus on the single focal plane.

Still another aspect of the present invention relates to a method and apparatus for sorting which includes aligning the respective selectively energizable second and fourth electromagnetic radiation emitters and associated selectively actuated electromagnetic radiation capturing devices with each other to focus on a single focal plane, and selectively energizing the respective second and fourth electromagnetic radiation emitters, and selectively actuating the associated electromagnetic radiation capturing devices, in a phase delayed operation on opposite sides of the product stream such that each selectively energizable electromagnetic radiation emitter does not destructively interfere with another selectively actuated electromagnetic radiation capturing device.

Still another aspect of the present invention relates to a method and apparatus for sorting wherein the predetermined pattern of energizing the respective selectively energizable first, second, third and fourth electromagnetic radiation emitters, and forming the interrogation signals with the associated selectively actuated electromagnetic radiation capturing devices further comprises first, energizing the first electromagnetic radiation emitter, and actuating the associated electromagnetic radiation capturing device for a first predetermined period of time; second, energizing the second electromagnetic radiation emitter and actuating the associated electromagnetic radiation capturing device for a second, predetermined time period; third, energizing the third electromagnetic radiation emitter, and actuating the associated electromagnetic radiation capturing device for a third, predetermined time period; and fourth, energizing the fourth electromagnetic radiation emitter and actuating the associated electromagnetic radiation capturing device for a fourth, predetermined time period that is phase delayed from, and partially overlapping with the second predetermined time period, and wherein the first, second and third predetermined time periods are sequential, in time, and the fourth predetermined time period partially overlaps, and extends from the second predetermined time period.

Still another aspect of the present invention relates to a method and apparatus for sorting wherein the step of selectively energizing the respective electromagnetic radiation emitters in a predetermined pattern, and selectively actuating the electromagnetic radiation capturing devices in the predetermined pattern takes place in a time interval of about 50 microseconds to about 500 microseconds.

Still another aspect of the present invention relates to a method and apparatus for sorting wherein the first predetermined time period is about 25 microseconds to about 250 microseconds; and the second predetermined time period is about 75 microseconds to about 150 microseconds; and the third predetermined time period is about 25 microseconds to about 250 microseconds; and the fourth predetermined time period is about 75 microseconds to about 150 microseconds, and partially overlaps with the second predetermined time period and is further phase delayed by about 5 microseconds to about 25 microseconds and effectively extends from the second predetermined time period by about 5 microseconds to about 25 microseconds.

Still another aspect of the present invention relates to a method and apparatus for sorting wherein the first and third selectively energizable electromagnetic radiation emitters comprise pulsed light emitting diodes; and the second and fourth selectively energizable electromagnetic radiation emitters comprise laser scanners.

Still another aspect of the present invention relates to a method and apparatus for sorting wherein the respective selectively energizable electromagnetic radiation emitters, when energized, emit electromagnetic radiation which lies in a range of about 400 nanometers to about 1600 nanometers wavelength.

Still another aspect of the present invention relates to a method and apparatus for sorting wherein the step of conveying the product along a path of travel comprises providing a continuous belt conveyor having an upper and lower flight; and wherein the upper flight has a first intake end, and a second exhaust end; and positioning the first, intake end elevationally, above, the second, exhaust end.

Still another aspect of the present invention relates to a method and apparatus for sorting which includes conveying the product with the conveyor at a predetermined speed of about 3 meters per second to about 5 meters per second.

Still another aspect of the present invention relates to a method and apparatus for sorting wherein the product stream moves along a predetermined trajectory which is influenced, at least in part, by gravity which acts upon the unsupported product stream.

Still another aspect of the present invention relates to a method and apparatus for sorting which includes locating the product ejector about 50 millimeters to about 150 millimeters downstream of the inspection station.

Still another aspect of the present invention relates to a method and apparatus for sorting wherein the predetermined sequential time periods do not substantially overlap.

Still another aspect of the present invention relates to a method and apparatus for sorting wherein the multitude of external and internal characteristics of the plurality of individual items are humanly perceptible.

Still another aspect of the present invention relates to a method and apparatus for sorting wherein the multitude of external and internal characteristics of the plurality of individual items are machine perceptible.

Still another aspect of the present invention relates to a method and apparatus for sorting wherein the multitude of external and internal characteristics of the plurality of individual items are not humanly perceptible.

These and other aspects of the present invention will be discussed in greater detail hereinafter.

BRIEF DESCRIPTION OF THE DRAWINGS

Preferred embodiments of the invention are described below with reference to the following accompanying drawings.

FIG. 1E is a greatly simplified, schematic view of a first form of the present invention.

FIG. 1E1 is a greatly simplified, graphical depiction of the operation of the first form of the present invention.

DETAILED DESCRIPTION OF THE PREFERRED EMBODIMENTS

Figure 1A:
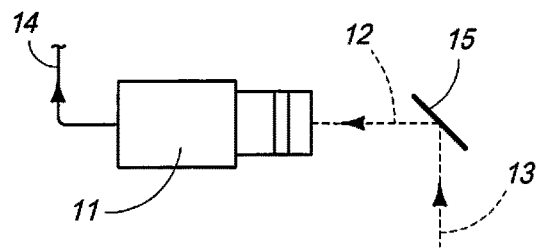
FIG. 1A is a greatly simplified, side elevation view of a camera located in spaced relation relative to a mirror.

This disclosure of the invention is submitted in furtherance of the constitutional purposes of the U.S. Patent Laws "to promote the progress of science and useful arts." (Article I, Section 8).

As noted earlier in the specification, the known benefits and relative strengths of camera imaging and laser scanning, and how these specific forms of product interrogation can be complimentary when used for product sorting applications are well known. It is now practical to combine high speed image data acquisition with sufficiently powerful computational and/or image processing capability to fuse multiple data streams in real-time, that is, with response times of several microseconds, to a few milliseconds, to generate useful images of objects traveling in a product stream. However, as noted, numerous problems exist when illuminators, emitters, detectors and/or interrogators of various designs are used in different modes of operation. It is well known that these modes of operation are often not normally or naturally compatible with each other without some loss of information or destructive signal interference. Furthermore, in optical applications, traditionally used means for spatially or spectrally separating signals often are not sufficient to isolate detector signals from destructive interference with each other. Consequently, the present application discloses a new way of controlling and acquiring multi-modal and multi-dimensional image features of objects requiring inspection. As noted above, it is well known that destructive interference often occurs between cameras and laser scanners which are operated simultaneously and in close proximity, or relative one to the other.

Those skilled in the art will recognize that spectral isolation is not practical for high order, flexible and/or affordable multi-dimensional detector or interrogator channel fusion. This is due, in large measure, to dichroic costs, and the associated sensitivity of angle of incidence and field angles relative to spectral proximity of desirable camera and laser scanner channels. Additional problems present themselves in managing "stacked tolerances" consisting of tightly coupled multi-spectral optical and optoelectronic components.

In addition to the problems noted earlier in this Application with regard to conventional detection and interrogation means used to inspect a stream of products, it is known that dynamic, spatial variances for products traveling as high speed bulk particulate, cannot be corrected or compensated, in real-time, by any conventional means. Consequently, traditional approaches to combine camera, and laser scanning through the separation, in time, or space, cannot support the generation of real-time pixel level, multi-modal image data utilization or fusion.

Those skilled in the art will recognize that the relationship between reflected, refracted, transmitted and absorbed electromagnetic energy, and these respective interactions with individual products moving in a product stream, provides assorted opportunities for non-destructive interrogation of individual objects moving in the stream, so as to determine the identity and quality of the product being inspected or sorted. Those skilled in the art will also recognize that there are known limits to acquiring reflected, refracted and transmitted electromagnetic radiation simultaneously. In particular, it's known that the product of reflection and transmission does not allow, under current conditions, measuring reflection and transmission of the electromagnetic radiation, independently. However, the present invention provides a solution to this dilemma, whereby, measured reflectance and measured transmission of electromagnetic radiation may be made substantially, simultaneously, and in real-time, so as to provide an increased level of data available and upon which sorting decisions can be made. In the present invention, the method and apparatus, as described, provides an effective means for forming, and fusing image channels from multiple detectors and interrogators using three approaches. These approaches include a spectral, spatial, and a temporal [time] approach. With regard to the first approach, that being a spectral approach, the present method and apparatus, is operable to allocate wavelengths of electromagnetic radiation [whether visible or invisible] by an appropriate selection of a source of electromagnetic radiation, and the use of optical filters. Further in this spectral approach, the provision of laser scanner and camera illumination spectra is controlled. Still further, a controller is provided, as will be discussed, hereinafter, and which is further operable to adjust the relative color intensity of camera illumination which is employed. Still further the spectral approach which forms and/or fuses inspection channels from multiple detectors, also coordinates the detection spectra so as to optimize contrast features, and the number of possible detector channels which are available to provide data for subsequent combination.

With regard to the spatial approach, as mentioned above, this approach, in combination with the spectral and temporal approaches, includes a methodology having a step of providing coincident views from the multiple electromagnetic radiation detecting devices to support inspection/image data acquisition or fusion. Secondly, the spatial approach includes a step for the separation of the multiple electromagnetic radiation detectors, and related detection zones to reduce destructive interference from electromagnetic radiation detectors having incompatible operational characteristics. Yet further, the spatial approach includes a step of adjusting the electromagnetic radiation emitter intensity, and shaping the electromagnetic radiation emissions to optimize field uniformity, and to further compensate for collection of electromagnetic radiation waves, which may be employed in the apparatus as described hereinafter.

With regard to the aforementioned temporal [time] approach to assist in the formation of a resulting fused inspection/image channels, the temporal approach includes the coordination of multiple inspections in a synchronous or predetermined pattern, and the allocation and phasing of data acquisition periods so as to isolate different inspection/imaging modes from substantial spectral overlap, and destructive interference, in a manner not possible heretofore. The temporal approach also includes a synchronized, phase adjusted, and pulsed (strobed) inspection/illumination, which is effective to isolate different inspection modes, again, from spectral overlap, and destructive interference. The present invention is operable to form real-time, multi-dimensional inspection from detection sources, which include different modes of sensing, and contrast generation, such that the resulting inspections include feature-rich contrasts and are not limited to red, green or blue and similar color spaces. Further, the present invention is not limited primarily to represent three dimensional spatial dimensions. Rather, the present invention fuses or joins together inspection data from multiple sources to generate high-order, multi-dimensional contrast features representative of the objects being inspected so as to better identify desired features, and constituents and the characteristics of the objects, and which can be utilized for more effective sorting of the stream of objects. The present invention as described, hereinafter, includes line scan or laser detectors, which correlate and fuse multiple channels of data having feature-rich object contrasts from streaming inspection data in real-time. This is in contrast to the more traditional approach of using two dimensional or area-array images, with or without lasers, as the basis for the formation of enhanced, three dimensional spatial or topographic inspection of individual objects moving within a stream of objects to be sorted.

Most importantly, the present invention, as described hereinafter, includes temporal [time] synchronization in combination with phase controlled, detector or interrogator isolation. This may be done in selective and variable combinations. While the present invention supports and allows for the use of more common devices such as optical beams splitters; spectra or dichroic filters; and polarization elements to isolate and combine the outputs of different detectors or interrogators, the present invention, in contrast, provides an effective means for separating and/or selectively and constructively combining inspection data from detection or interrogation sources that would otherwise destructively interfere with each other. As indicated earlier, while prior art methods are in existence, which employ beam splitters, dichroic spectral filters, and/or polarizing elements in various ways, these devices, and the associated methodology associated with their utilization, both individually, and in combination with each other, have many undesirable effects and limitations including, but not limited to, a lack of isolation of signals of different modes, but similar optical spectrum; unwanted change in a response per optical angle of incidence, and field angles; and/or a severe loss of sensitivity or affected dynamic range.

The apparatus and method of the present invention is generally indicated by the numeral 10 in FIG. 1A, and following. Referring now to FIG. 1A, the apparatus and method 10 of the present invention includes an electromagnetic radiation detector, here shown as a camera 11 of traditional design. The camera has an optical axis which is generally indicated by the numeral 12. The optical axis, receives reflected electromagnetic radiation 13. Upon receiving the reflected electromagnetic radiation 13, which may be visible or invisible, the camera 11 produces a device signal 14, which is subsequently provided to an image pre-processor, which will be discussed in greater detail, below. In the arrangement as seen in FIG. 1A, a mirror 15 is provided, and which is utilized to direct or reflect electromagnetic radiation 13 along the optical axis 12 of the camera 11, so that the camera can form an appropriate device signal representative of the electromagnetic radiation, which has been collected.

Figure 1B:
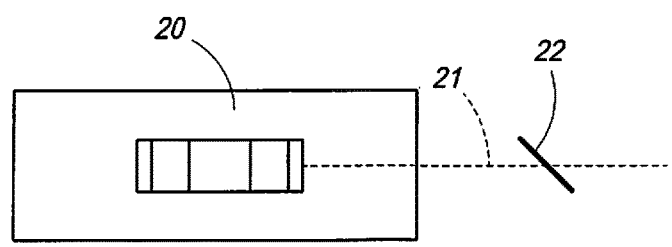
FIG. 1B is a greatly simplified, schematic view of a laser scanner, and a dichroic beam mixing optical element.

Referring now to FIG. 1B, the present apparatus and method 10 includes, in some forms of the invention, another form of electromagnetic radiation detector, here shown as a laser or line scanner of traditional design, and which is generally indicated by the numeral 20. The laser scanner has an optical axis which is indicated by the numeral 21. Still further, and in one possible form of the invention, a dichroic beam mixing optical element 22 of traditional design is provided, and which is operable to act upon the reflective electromagnetic radiation 13, as will be described hereinafter so as to provide reflected electromagnetic radiation 13, which is then directed along the optical axis 12 of the camera 11.

Figure 1C:
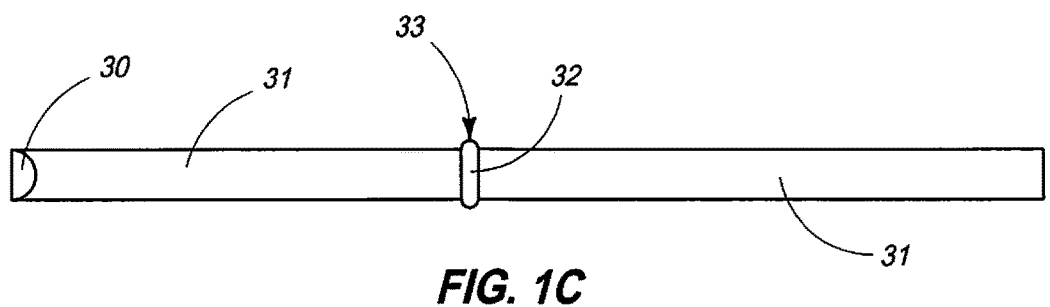
FIG. 1C is a greatly simplified, schematic representation of an electromagnetic radiation emitter emitting a beam of visible or invisible electromagnetic radiation, and wherein a detector focal plane is graphically depicted in spaced relation relative to the electromagnetic radiation emitter and along the emitted beam.
Figure 1D:
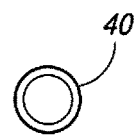
FIG. 1D is a greatly simplified depiction of a background element which as illustrated in the drawings, hereinafter, can be either passive, that is, no electromagnetic radiation is emitted by the background; or active, that is, the background can emit electromagnetic radiation, which is visible, or invisible.

Referring now to FIG. 1C, the present apparatus and method 10 includes a multiplicity of electromagnetic radiation emitters, here shown as illumination devices which are generally indicated by the numeral 30. The multiplicity of illumination devices 30 may be located at various positions and at various orientations so as to provide the desired illumination. In this quite simplistic view, the respective illumination devices 30, when energized during predetermined time intervals, each produce a beam of electromagnetic radiation 31 [which may be collimated or not collimated] and which is directed towards a location of a detector and/or interrogator focal plane, and which is generally indicated by the numeral 32. The location of the detector or interrogator focal plane 32 represents an orientation or location where a stream of objects to be inspected passes therethrough. The focal plane 32 is located within an inspection station 33, as will be discussed in further detail, below. In the drawings, as provided, it will be recognized that the present apparatus and method 10 includes a background, which is generally, and simply illustrated by the numeral 40 in FIG. 1D. The background 40 is well known. The background 40 is located along the optical axis of the camera 11, and the laser scanner 20. The background 40, which is provided, can be passive, that is, the background emits no electromagnetic radiation, which is visible or invisible, or, on the other hand, the background 40 may be active, that is, it may be selectively energized to emit electromagnetic radiation, which may be either visible or invisible, depending upon the sorting application being employed.

Referring now to FIG. 1E a first form of the invention 41 is illustrated. In its most simplistic form, the invention 10 includes electromagnetic radiation detectors, shown as a camera 11, and a laser scanner 20, which are positioned on one side of an inspection station 33. Plural electromagnetic radiation emitters, shown as illumination devices 30 are provided, and which are also located on one side of the inspection station. As illustrated, the background 40 is located on the opposite side of the inspection station 33. Electromagnetic radiation (light) which is generated by the illuminators 30, is directed toward the focal plane 32. Further, objects requiring inspection pass through the inspection station 33, and reflected electromagnetic radiation 13 from the objects are received by the electromagnetic radiation detectors 11, 20. Referring now to FIG. 1E1, a graphical depiction of the first form of the invention 41 is illustrated. As will be appreciated, the methodology includes a step of energizing the electromagnetic radiation detector camera 11 during two discrete time intervals, which are both before, and after, the electromagnetic radiation detector laser scanner 20 is rendered operable. This temporal activity of the camera 11 and laser scanner 20 prevents any destructive interference of the devices 11, and 20, one with the other.

Figure 2:
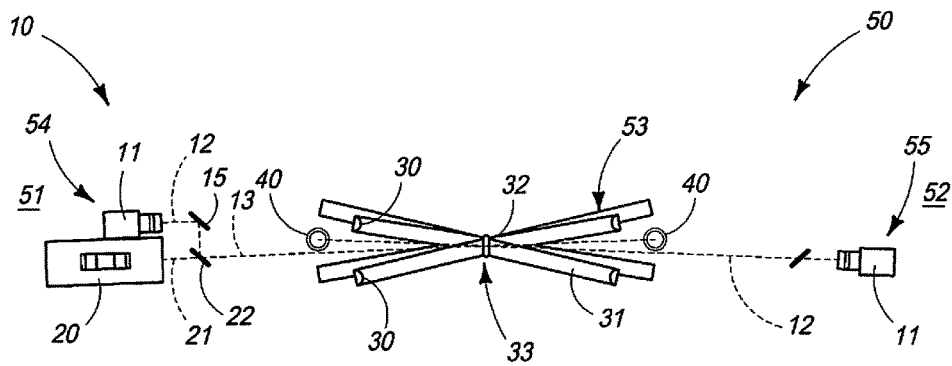
FIG. 2 is a greatly simplified, side elevation view of a second form of the present invention.
Figure 2A:
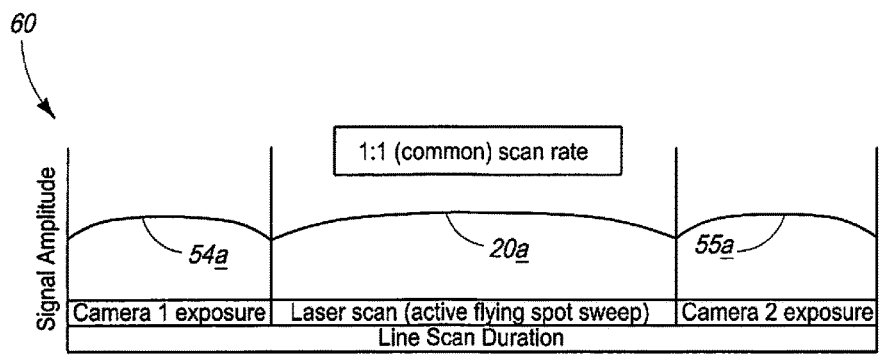
FIG. 2A is a greatly simplified, graphical depiction of the second form of the invention during operation.
Figure 2B:
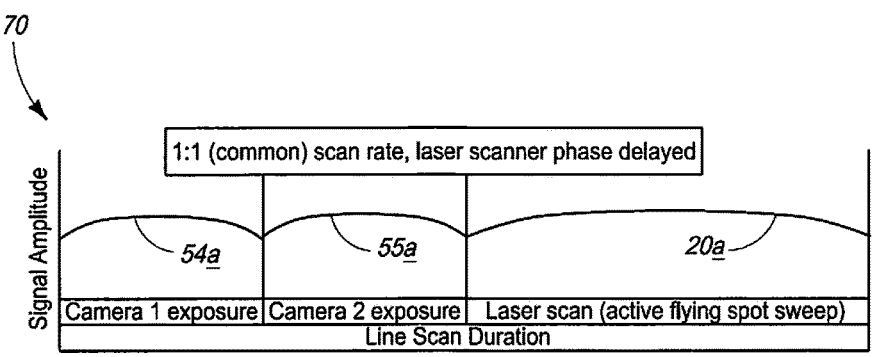
FIG. 2B is a greatly simplified, graphical depiction of a second mode of operation of the second form of the invention.

Referring now to FIG. 2, the second form of the invention 50 is shown, and which is operable to interrogate a stream of products, as will be discussed, below. It should be understood that the earlier-mentioned inspection station 33, through which a stream of products pass to be inspected, or interrogated, has opposite first and second sides 51 and 52, respectively, and which are spaced from the focal plane 32. In the second form of the invention 50, a multiplicity of electromagnetic radiation emitters 53 are positioned on the opposite first and second sides 51 and 52 of the inspection station 33, and are oriented so as to generate waves of electromagnetic radiation 31, and which are directed at the focal plane 32, and through which the stream of the products pass for inspection. In the arrangement as seen in FIG. 2, the second form of the invention 10 includes a first camera detector 54, and a second camera detector 55, which are located on the opposite first and second sides 51 and 52 of the inspection station 33. As can be seen by an inspection of the drawings, the optical axis of the respective electromagnetic radiation detector cameras 11, which are used in this form of the invention, are directed to the focal plane 32, and through which the objects to be inspected pass, and further extends to the background 40. Referring now to FIG. 2A, a first mode of operation 60, of the invention arrangement, is illustrated. In this graphical depiction, the temporal actuation of the respective cameras 54 and 55, respectively, as depicted in FIG. 2, is shown. The respective camera energizing or exposure time is plotted as against signal amplitude as compared with the electromagnetic radiation detector laser scanner mentioned earlier, and which is indicated by the numeral 20. As can be seen, the electromagnetic radiation detector camera actuation or exposure time is selected so as to achieve a one-to-one (1:1) common scan rate with the electromagnetic radiation detector laser scanner 20. As will be recognized, the exposure time for electromagnetic radiation detector cameras 1 and 2 (54 and 55) equals the active time period during which the electromagnetic radiation detector laser scanner 20 is operational. As will be recognized, the signal amplitude of the first electromagnetic radiation detector camera is indicated by the numeral 54($a$). The signal amplitude of the electromagnetic radiation detector laser scanner 20 is indicated by the numeral 20($a$) and the signal amplitude of the second electromagnetic radiation detector camera 55 is indicated by the numeral 55($a$). Referring again to FIG. 2, and as a second possible mode of operation for the form of the invention, as seen in FIG. 2, an alternative arrangement for the actuation or exposure of the electromagnetic radiation detector cameras 54 and 55 are provided relative to the duration and/or operation of the electromagnetic radiation detector laser scanner 20. Again, the duration of the respective exposures of the electromagnetic radiation detector cameras 54 and 55 is equal to the duration of the active electromagnetic radiation detector laser scanner 20 operation as provided. In the arrangement as seen in FIG. 2B, it will be recognized that in the second mode of operation 70, the laser scanner 20, is actuated in a phase-delayed mode; however, in the mode of operation 70 as graphically depicted, a 1:1, a common scan rate is achieved.

Figure 3:
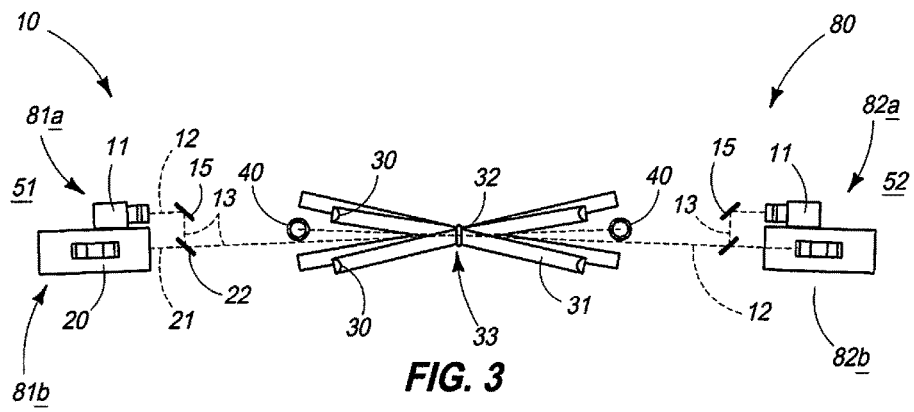
FIG. 3 is a greatly simplified, graphical depiction of a third form of the present invention.
Figure 3A:
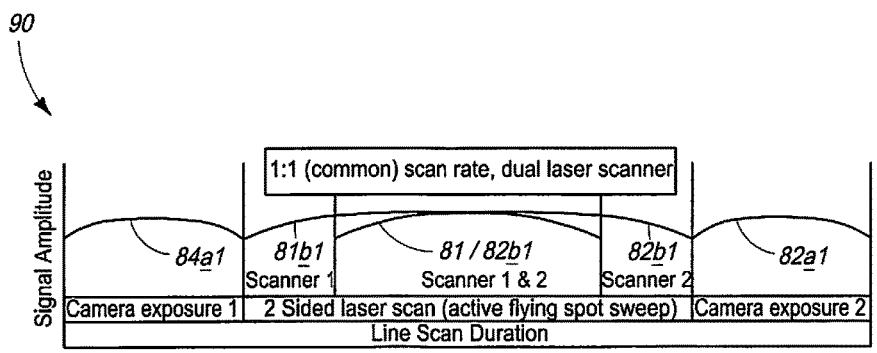
FIG. 3A is a greatly simplified, graphical depiction of the operation of the third form of the invention as depicted in FIG. 3.
Figure 3B:
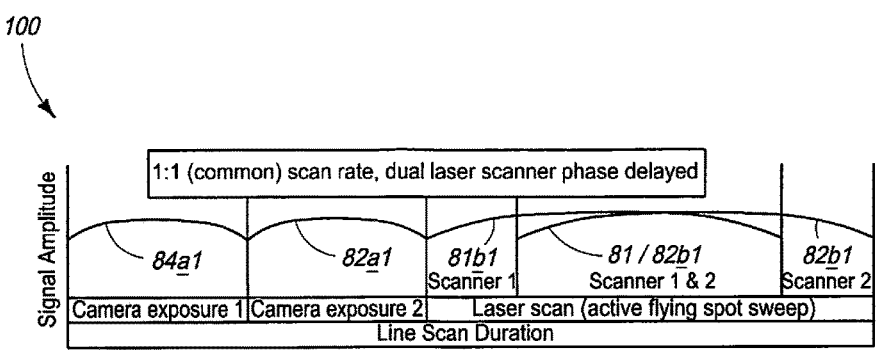
FIG. 3B is a greatly simplified, graphical depiction of the operation of the present invention as shown in FIG. 3 during a second mode of operation.

Turning now to FIG. 3, a third form of the invention 80 is illustrated in a quite simplistic form. The third form of the invention 80 includes a first electromagnetic radiation detector camera and electromagnetic radiation detector laser scanner combination indicated by the numerals 81a and 81b respectively, and which are positioned at the first side 51, of the inspection station 33. Still further, the third form of the invention includes a second electromagnetic radiation detector camera and electromagnetic radiation detector laser scanner combination 82a and 82b, respectively. Again, in the third form of the invention 80, multiple electromagnetic radiation emitter illumination devices 30, of varying wavelengths, are provided, and which are selectively, electrically actuated so as to produce electromagnetic radiation 31, which is directed towards the focal plane 32. Referring now to FIG. 3A, a first mode of operation 90, for the form of the invention 80, as seen in FIG. 3, is graphically depicted. It will be recognized that the combinations of the first and second electromagnetic radiation detector cameras 81a and 82a, along with electromagnetic radiation detector laser scanners 81b and 82b as provided, provide a 1:1 scan rate. Again, when studying FIG. 3A, it will be recognized that the actuation or exposure of the respective electromagnetic radiation detector cameras 81a and 82a, respectively, is equal to the time duration that the electromagnetic radiation detector laser scanners 81b and 82b, respectively, are operational. The signal amplitude of the first electromagnetic radiation detector camera is indicated by the numeral 81a1, and the signal amplitude of the electromagnetic radiation detector laser scanner 81b is indicated by the numeral 81b1. Still further, the signal amplitude of the second electromagnetic radiation detector camera 82a is indicated by the numeral 82a1, and the signal duration of the second electromagnetic radiation detector laser scanner is indicated by the numeral 82b1. Another alternative mode of operation is indicated by the numeral 100 in FIG. 3B. However in this arrangement, while a 1:1 common scan rate is achieved, the dual electromagnetic radiation detector laser scanners 81b and 82b, respectively, are phase delayed.

Figure 4:
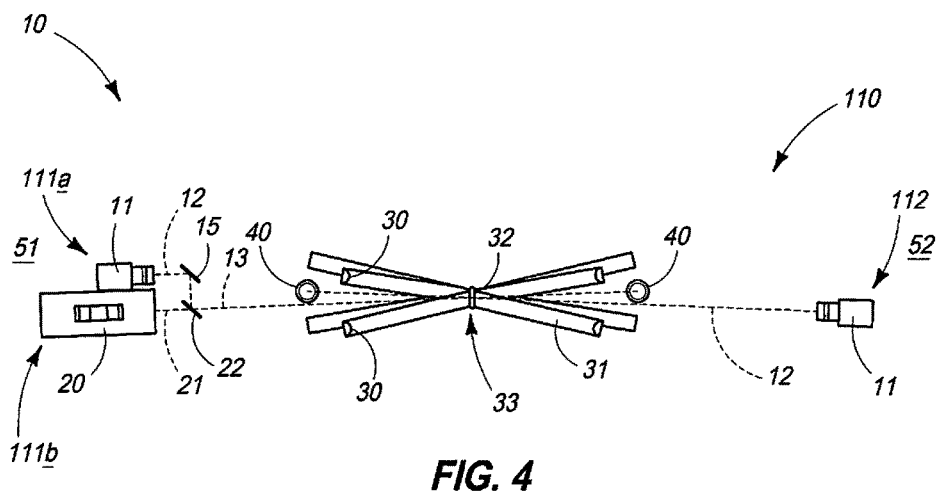
FIG. 4 is still another, greatly simplified, side elevation view of yet another form of the present invention.
Figure 4A:
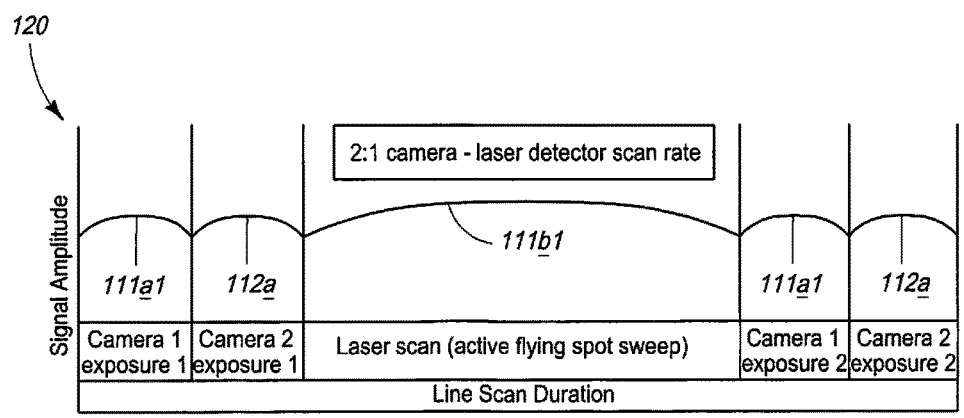
FIG. 4A is a greatly simplified, graphical depiction of the operation of the invention as seen in FIG. 4.

Referring now to FIG. 4, a fourth form of the invention is generally indicated by the numeral 110. In the arrangement, as seen in FIG. 4, a first electromagnetic radiation detector camera and electromagnetic radiation detector laser scanner combination are generally indicated by the numerals 111a and 111b, respectively, are provided, and which are positioned on one of the opposite sides 51 and/or 52 of the inspection station 33. In this arrangement a second electromagnetic radiation detector camera 112 is positioned on the opposite side of the inspection station. In the mode of operation as best seen in the graphical depiction as illustrated in FIG. 4A, a 2:1 electromagnetic radiation detector camera-laser scanner detection scan rate is achieved. The signal amplitude of the first electromagnetic radiation detector camera 111a is indicated by the numeral 111a1, and the signal amplitude of the electromagnetic radiation detector laser scanner 111b is indicated by the numeral 111b1. Still further, the signal amplitude of the second electromagnetic radiation detector camera 112 is illustrated in FIG. 4A, and is indicated by the numeral 112a. Again, by a study of FIG. 4A, it will be recognized that the respective electromagnetic radiation detector cameras and electromagnetic radiation detector laser scanners, which are provided, can be selectively actuated during predetermined time periods to achieve the benefits of the present invention, which include, but are not limited to, preventing destructive interference of the respective electromagnetic radiation detector scanners or electromagnetic radiation detector cameras when viewing or interrogating a stream of objects passing through the inspection station 33, as will be described, below.

Figure 5:
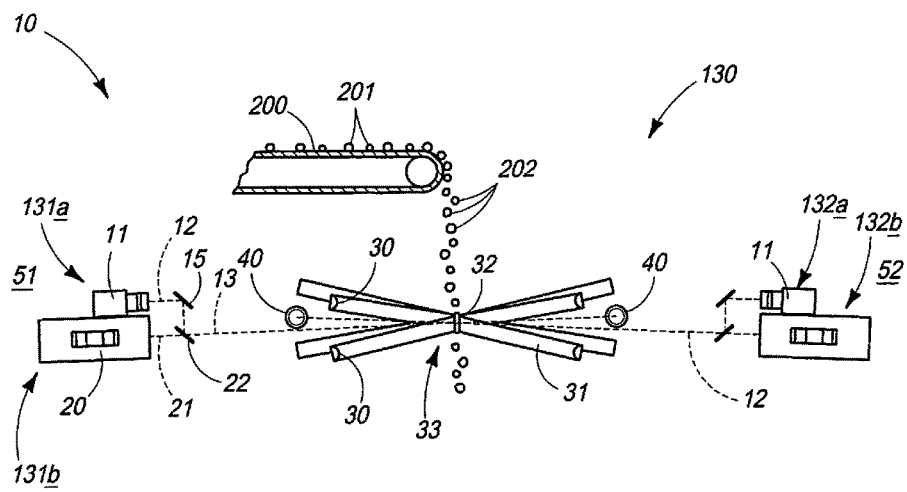
FIG. 5 is a greatly simplified, side elevation view of yet another form of the present invention.
Figure 5A:
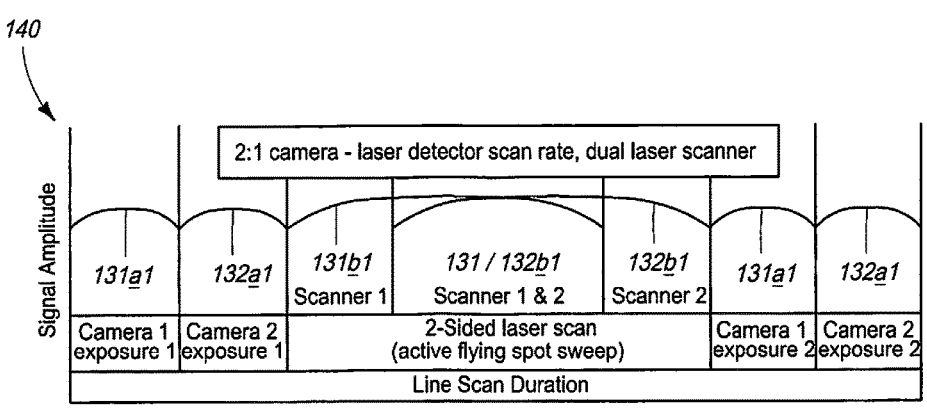
FIG. 5A is a greatly simplified, graphical depiction of the operation of the form of the invention as seen in FIG. 5.

Referring now to FIG. 5, a fifth form of the invention is generally indicated by the numeral 130. In this arrangement, which implements the methodology of the present invention, a first electromagnetic radiation detector camera and electromagnetic radiation detector laser scanner combination, are indicated by the numerals 131a and 131b, respectively, are provided. The first electromagnetic radiation detector camera and electromagnetic radiation detector line or laser scanner combination 131a and 131b are located on one side of the inspection station 33. Still further in this form of the invention 130, a second electromagnetic radiation detector camera and electromagnetic radiation detector laser scanner combination is indicated by the numerals 132a and 132b, respectively. The second electromagnetic radiation detector camera and electromagnetic radiation detector laser scanner combination is located on the opposite side of the inspection station 33. During one possible mode of operation of the invention, which is seen in FIG. 5A, and which is indicated by the numeral 140, the signal amplitude of the respective first and second electromagnetic radiation detector camera and electromagnetic radiation detector laser scanner combination, as described above, is shown. In the mode of operation 140 as depicted, a 2:1 electromagnetic radiation detector camera-laser detection scan rate is achieved, utilizing this dual electromagnetic radiation detector camera, dual laser scanner arrangement. Again by studying FIG. 5A, it can be seen that the individual electromagnetic radiation detector cameras and electromagnetic radiation detector laser scanners, as provided, can be selectively, electrically energized so as to provide a data stream such that the individual electromagnetic radiation detectors/interrogators/cameras, as provided, do not interfere with the operation of other electromagnetic radiation detectors/cameras which are rendered operational while the product stream is passing through the inspection station 33.

Figure 6:
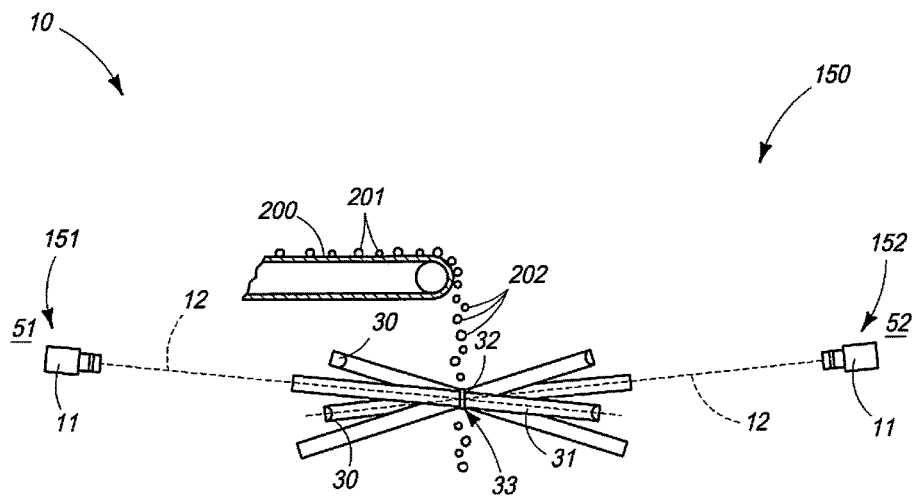
FIG. 6 is a greatly simplified, side elevation view of yet another form of the present invention.
Figure 6A:
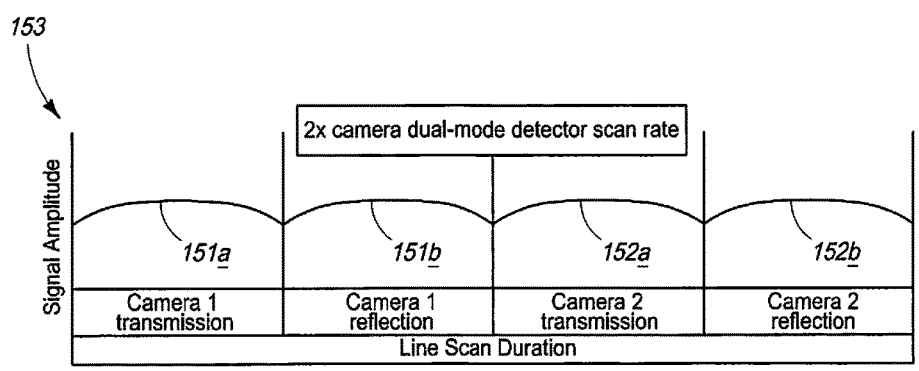
FIG. 6A is a greatly simplified, graphical depiction of the operation of the present invention as seen in FIG. 6.

Referring now to the sixth form of the invention, as seen in FIG. 6, the sixth form of the invention 150 includes first and second electromagnetic radiation detector cameras, which are indicated by the numerals 151 and 152, respectively, and which are positioned on opposite sides of the inspection station 33. The respective electromagnetic radiation detector cameras 151 and 152 have two modes of operation, that being a transmission mode, and a reflective mode. As seen in FIG. 6A, the mode of operation of the sixth form of the invention 150 is graphically illustrated. In this form of the invention the two electromagnetic radiation detector cameras 151 and 152 are operated in a dual-mode detector scan rate. It will be noted that the duration of the electromagnetic radiation detector camera actuation for transmission and reflection is substantially equal in time. The signal amplitude of the first electromagnetic radiation detector camera transmission mode is indicated by the line labeled 151a, and the signal amplitude of the first electromagnetic radiation detector camera reflection mode is indicated by the numeral 151*b*. Similarly, the signal amplitude of the second electromagnetic radiation detector camera transmission mode is indicated by the numeral 152*a*, and the signal amplitude of the second electromagnetic radiation detector camera reflection mode is indicated by the numeral 152*b*. Again, the respective electromagnetic radiation detector cameras, as disclosed in this paragraph, are operated in a temp oral manner so as to prevent interference with other electromagnetic radiation detectors and operations taking place, simultaneously.

Figure 7:
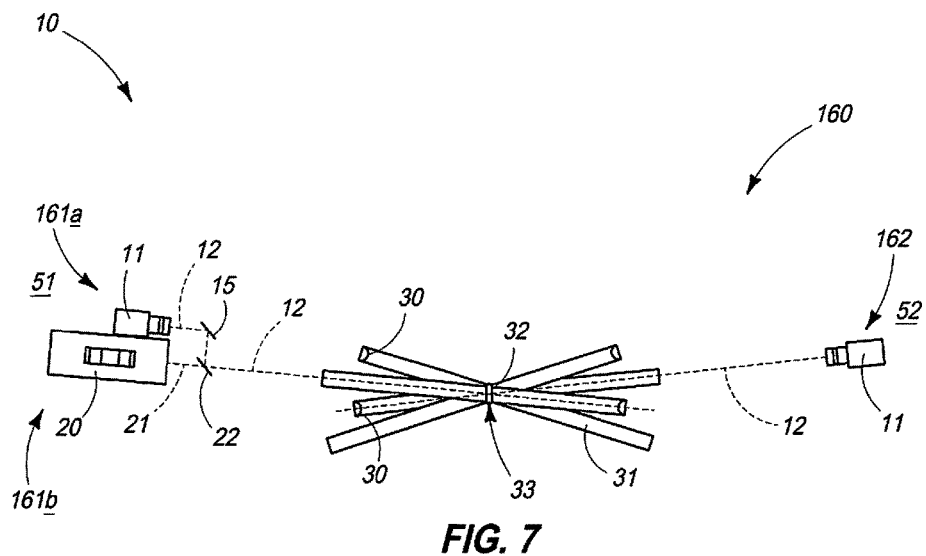
FIG. 7 is a greatly simplified, side elevation view of yet another form of the present invention.
Figure 7A:
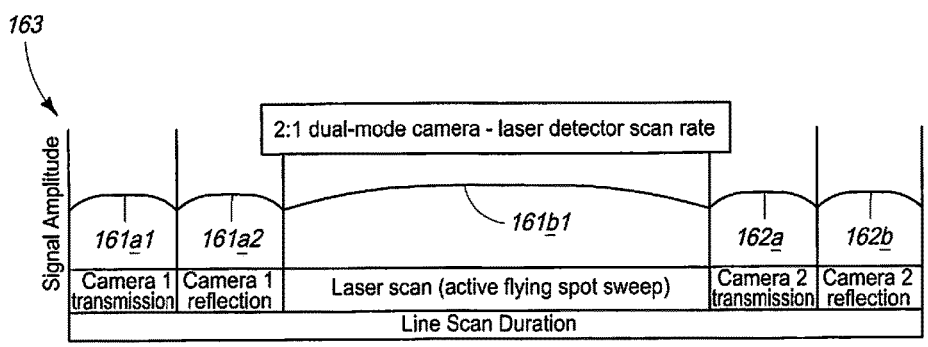
FIG. 7A is a greatly simplified, graphical depiction of the operation of the present invention as seen in FIG. 7.

Referring now to FIG. 7, a seventh form of the invention is generally indicated by the numeral 160 therein. In this greatly simplified form of the invention, a first electromagnetic radiation detector camera, and first electromagnetic radiation detector laser scanner combination 161*a* and 161*b* are provided, and which are positioned on one side of the inspection station 33. On the opposite side thereof, a second electromagnetic radiation detector camera 162 is provided. Referring now to FIG. 7A, and in one mode of operation 163 of the arrangement as seen in FIG. 7, the mode of operation 163 is graphically depicted as a 2:1 dual-mode electromagnetic radiation detector camera and electromagnetic radiation detector laser scanner arrangement. As seen in FIG. 7A, the respective electromagnetic radiation detector cameras 161A and 162, respectively, can be operated in either a transmission or reflection mode. As will be recognized by a study of FIG. 7A, the signal amplitude of the first electromagnetic radiation detector camera 161*a* in the transmission mode, is indicated by the numeral 161*a*1, and the signal amplitude of the reflective mode of the first electromagnetic radiation detector camera is indicated by the numeral 161*a*2. Further, the signal amplitude of the first electromagnetic radiation detector laser scanner 161*b*, is indicated by the numeral 161*b*1; and the signal amplitude of the transmission mode of the second electromagnetic radiation detector camera is indicated by the numeral 162*a*. The signal amplitude of the reflective mode of the second electromagnetic radiation detector camera is indicated by the numeral 162*b*. Again, the advantages of the present invention 10 relates to the selective actuation of the respective components, as described herein, so as to prevent destructive interference while the specific electromagnetic radiation detectors/sensors/interrogators are rendered operable to inspect or interrogate a stream of products passing through the inspection station 33.

Figure 8:
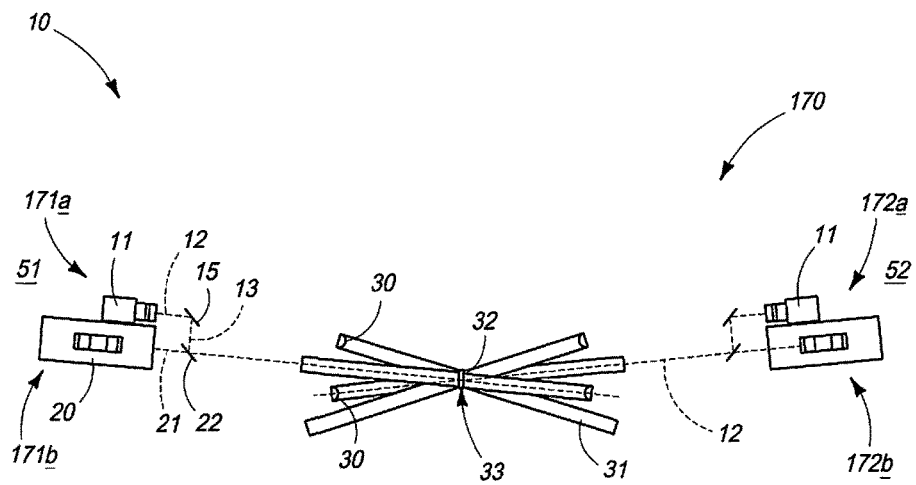
FIG. 8 is a greatly simplified, side elevation view of yet another form of the present invention.
Figure 8A:
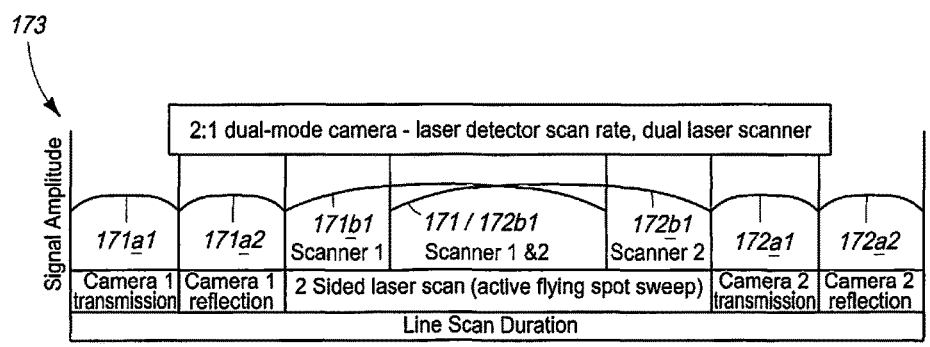
FIG. 8A is a greatly simplified, graphical depiction of the present invention as seen in FIG. 8 during operation.

Referring now to FIG. 8, an eighth form of the invention is generally indicated by the numeral 170. The eighth form of the invention includes, as a first matter, a first electromagnetic radiation detector camera 171*a*, and first electromagnetic radiation detector laser scanner 171*b*, which are each positioned in combination, and on one side of the inspection station 33. Further, a second electromagnetic radiation detector camera and second electromagnetic radiation detector laser scanner combination 172*a* and 172*b*, respectively, are located on the opposite side of the inspection station 33. As seen in FIG. 8A, a mode of operation is graphically depicted for the eighth form of the invention 170. As seen in that graphic depiction, a 2:1 dual mode electromagnetic radiation detector camera-laser detector scan rate, and dual electromagnetic radiation detector laser scanner operation can be conducted. As with the other forms of the invention, as previously illustrated, and discussed, above, the first electromagnetic radiation detector camera 171*a*, and second electromagnetic radiation detector camera 172*a*, each have a transmission and reflection mode of operation. Consequently, when studying FIG. 8A, it will be appreciated that the line labeled 171*a*1 represents the signal amplitude of the first electromagnetic radiation detector camera transmission mode, and the line labeled 171*a*2 is the first electromagnetic radiation detector camera reflection mode. Similarly, the signal amplitude of the second electromagnetic radiation detector camera transmission mode is indicated by the line labeled 172*a*1, and the second electromagnetic radiation detector camera reflection mode is indicated by the line labeled 172*a*2. The signal amplitude, over time, of the respective components, and in particular the first and second electromagnetic radiation detector laser scanners, are indicated by the numerals 171*b*1 and 172*b*1, respectively.

Figure 9:
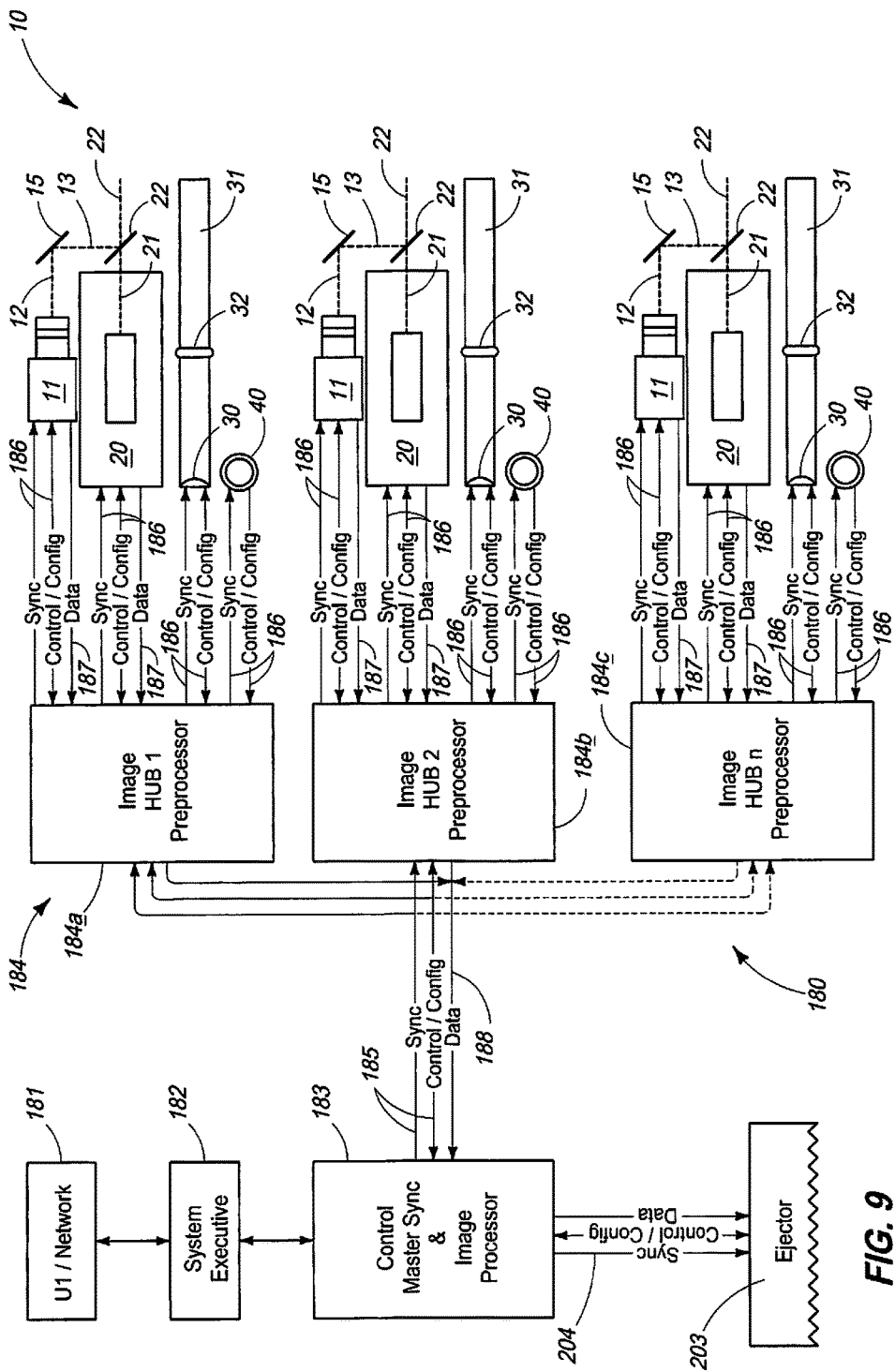
FIG. 9 is a greatly simplified, schematic diagram showing the major components, and working relationship of the components of the present invention which implement the methodology as described, hereinafter.
Figure 10:
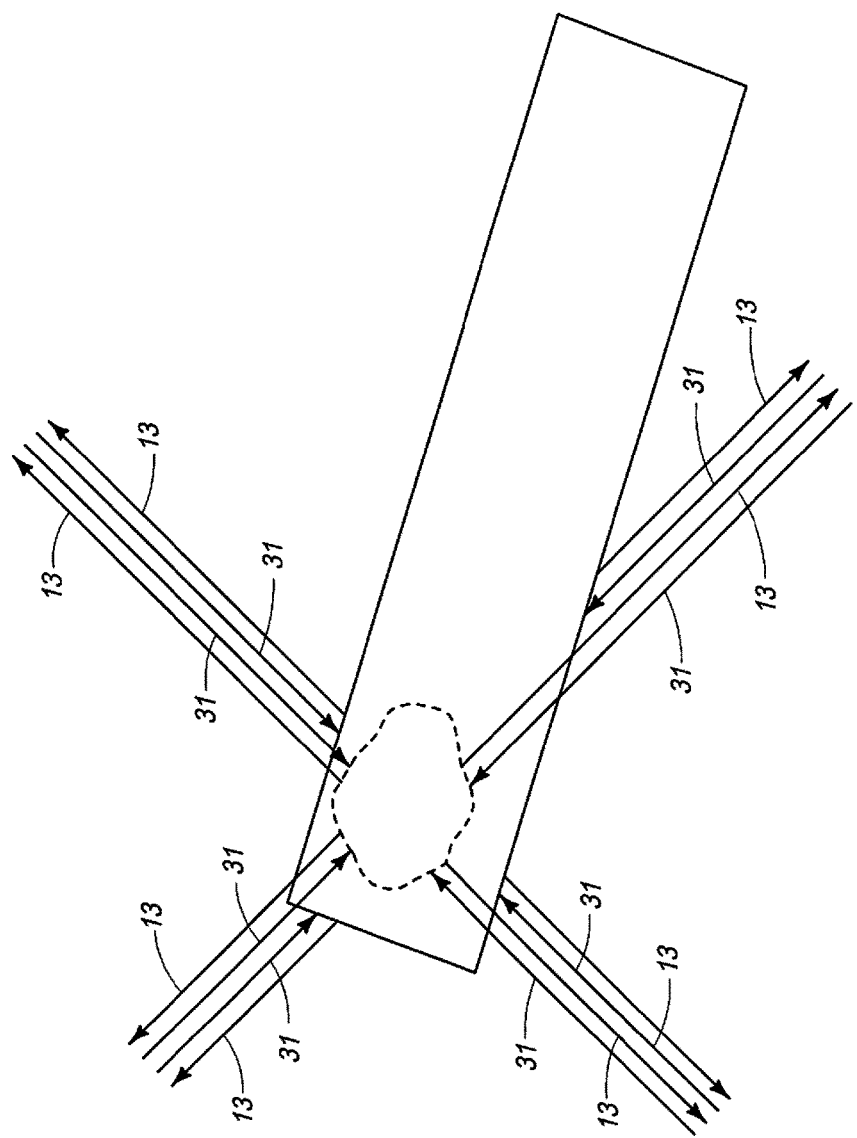
FIG. 10 is a greatly simplified graphical representation of an individual item of interest being irradiated by electromagnetic radiation from various directions, and showing the electromagnetic radiation waves being reflected from both external characteristics of the individual item of interest, and also from internal characteristics of the individual item of interest.

Referring now to FIG. 9, a greatly simplified schematic view is provided, and which shows the operable configuration of the major components of the present apparatus, and which is employed to implement the methodology of the present invention 10. With regard to FIG. 9, it will be recognized that the apparatus and methodology 10 includes a user interface or network input device, which is coupled to the apparatus 10, and which is used to monitor operations and make adjustments in the steps of the methodology, as will be described, below. The control arrangement, as seen in FIG. 9, and which is indicated by the numeral 180, includes the user interface 181, and which provides control and configuration data information, and commands to the apparatus 10, and the methodology implemented by the apparatus. The user interface is directly, electrically coupled either by electrical conduit, or by wireless signal to a system executive, which is a hardware and software device, which is used to execute commands provided by the user interface. The system executive provides controlling and configuration information, and a data stream, and further is operable to receive images processed by a downstream image processor, and master synchronous controller which is generally indicated by the numeral 183. As should be understood, the "System Executive" hosts the user interface, and also directs the overall, but not real-time, operation of the apparatus 10. The System Executive stores assorted, predetermined, executable programs which cause the selective activation of the various components which have been earlier described. The controller 183 is operable to provide timed, synchronous signals or commands in order to actuate the respective electromagnetic radiation detector cameras 11, electromagnetic radiation detector laser scanners 20, electromagnetic radiation emitter illumination assemblies 30, and backgrounds 40 as earlier described, in a predetermined order, and over given time periods so as to effect the generation of device signals, as will be discussed below, and which can then be combined and manipulated by multiple image preprocessors 184, in order to provide real-time data, which can be assembled into a useful data stream, and which further can provide real-time information regarding internal and external features and characteristics of the stream of products moving through the inspection station 33. As indicated above, the present control arrangement 180 includes multiple image preprocessors here indicated by the numerals 184*a*, 184*b* and 184*c*, respectively. As seen in FIG. 9, the command and control, and synchronous control information is provided by the controller 183, and is supplied to each of the image preprocessors 184*a*, 184*b* and 184*c*, respectively. Further it will be recognized that the image preprocessors 184*a*, 184*b* and 184*c* then provide a stream of synchronous control, and control and configuration data commands to the respective assemblies, such as the electromagnetic radiation detector camera 11, electromagnetic radiation detector laser scanner 20, electromagnetic radiation emitter illumination device 30, or background 40, as individually arranged, in various angular, and spatial orientations on opposite sides of the inspection station 30. This synchronous, and control and configuration data allows the respective devices, as each is described, above, to be switched to different modes; to be energized and de-energized in different time sequences; and further to be utilized in such a fashion so as to prevent any destructive interference from occurring with other devices, such as electromagnetic radiation detector cameras 11, electromagnetic radiation detector laser scanners 20 and other electromagnetic radiation emitter illumination devices 30, which are employed in the present invention 10. When rendered operational, the various electrical devices, and sensors which include electromagnetic radiation detector cameras 11; electromagnetic radiation detector laser scanners 20; electromagnetic radiation emitter illumination devices 30; and backgrounds 40, provide device signals 187, which are delivered to the individual image preprocessors 184a, 184b and 184c, and where the image pre-processors are subsequently operable to conduct operations on the supplied data in order to generate a resulting data stream 188, which is provided from the respective image pre-processors 184a, 184b and 184c the controller 183 and image processor. The image processor and controller 183 is then operable to effect a decision making process in order to identify defective or other particular features of individual products passing through the inspection station 33, and which could be either removed by an ejection assembly, as noted below, or further diverted or processed in a manner appropriate for the feature identified, such as for sorting the objects by grade or predetermined quality characteristics.

As seen in the drawings, the current apparatus and method 10 includes, in one possible form, a conveyor 200 for moving individual products 201 in a nominally continuous bulk particulate stream 202, along a given path of travel, and through one or more automated inspection stations 30, and one or more automated ejection stations 203. As seen in FIG. 9, the ejection station 203 is coupled in signal receiving relation 204 relative to the controller 183. The ejection station 203 is equipped with an air ejector of traditional design, and which removes predetermined products from a product stream through the release of pressurized air.

A sorting apparatus 10 for implementing the steps, which form the methodology of the present invention, are seen in FIG. 1A and following. In this regard, the sorting apparatus and method 10, of the present invention, includes a source of individual products 201, and which have multiple distinguishing features. Some of these features may be hidden or internal or otherwise may not be easily discerned visually, in real-time in a fast moving product stream. The sorting apparatus 10 further includes a conveyor 200 for moving the individual products 201, in a nominally continuous bulk particulate stream 202, and along a given path of travel, and through one or more automated inspection stations 33, and one or more automated ejection stations 203. The sorting apparatus 10 further includes a plurality of selectively energizable electromagnetic radiation emitter illumination devices 30, and which are located in different spaced, angular orientations in the inspection station 33, and which, when energized, emit electromagnetic radiation 31 of varying wavelengths, which is directed toward the stream of individual products 202, such that the electromagnetic radiation 31 is reflected, refracted, transmitted or absorbed by the individual products 201, as they pass through the inspection station 33. The apparatus 10 further includes a plurality of selectively operable electromagnetic radiation detection devices 11, and 20, which are located in different, spaced, angular orientations in the inspection station 33. The electromagnetic radiation detection devices provide multiple modes of non-contact, non-destructive interrogation of reflected, refracted or transmitted electromagnetic radiation 31, to identify various features and characteristics (internal and external) of the respective products 201. Some of the multiple modes of non-contact, non-destructive product interrogation, if operated continuously, simultaneous and/or coincidently, would destructively interfere with other interrogation signals formed from the products 201, which are interrogated. The apparatus 10 further includes a configurable, programmable, multi-phased, synchronizing interrogation signal acquisition controller 183, and which further includes an interrogation signal data processor and which is operably coupled to the electromagnetic radiation emitter illumination and electromagnetic radiation detection devices 11, 20 and 30, respectively, so as to selectively activate electromagnetic radiation emitter illuminators 30, and electromagnetic radiation detectors 11 and 20, in a programmable, predetermined order which is specific to the products 201 which are being inspected. This avoids the possibility of destructive simultaneous interrogation signal interference, and preserves spatially correlated, and pixilated, real-time, interrogation signal data from each actuated electromagnetic radiation detector 11 and 20, and which is supplied to the controller 183, as the products 201 pass through the inspection station 33. In the arrangement as seen in the drawings, the integrated image data preprocessor 184 combines the respective device signals 187 through a sub-pixel level correction of spatially correlated image data from each actuated electromagnetic radiation detector 11, 20 to form real-time, continuous, multi-modal, multi-dimensional digital images 188 representing the product flow 202, and in which multiple dimensions of the digital data, indicating distinguishing features and characteristics of said products, is generated. The apparatus 10 also includes a configurable, programmable, real-time, multi-dimensional interrogation signal data processor 182, and which is operably coupled to the controller 183, and image pre-processor 184. This assembly identifies products 201, and product features and characteristics from contrasts, gradients and pre-determined ranges, and patterns of values specific to the products 201 being interrogated, and which is generated from the pre-processed continuous interrogation data. Finally, the apparatus has one or more spatially and temporally targeted ejection devices 203, which are operably coupled to the controller 183 and processor 182 to selectively redirect selected products 201 within the stream of products 202, as they pass through an ejection station 203.

OPERATION

The operation of the described embodiments of the present invention are believed to be readily apparent and are briefly summarized at this point. In its broadest aspect, the methodology of the present invention includes the steps of providing a stream 202 of individual products 201 to be sorted, and wherein the individual products 201 have a multitude external and internal of characteristics that are perceptible. The methodology of the present invention includes a second step of moving the stream of individual products 201 through an inspection station 33. Still another step of the present invention includes providing a plurality of electromagnetic radiation detection devices 11 and 20, respectively, in the inspection station for identifying the multitude of external and internal features and characteristics of the individual products. The respective electromagnetic radiation detection devices, when actuated, generate device signals 187, and wherein at least some of the plurality of electromagnetic radiation detection devices 11 and 20, if actuated, simultaneously, interfere in the operation of other actuated electromagnetic radiation detection devices. The methodology includes another step of providing a controller 183 for selectively actuating the respective electromagnetic radiation detection devices 11, 20 and 30, respectively, in a pre-determined order, and in real-time, so as to prevent interference in the operation of the selectively actuated electromagnetic radiation detection devices. The methodology includes another step of delivering the electromagnetic radiation detection device signals 187 which are generated by the respective electromagnetic radiation detection devices, to the controller 183. In the methodology of the present invention, the method includes another step of forming a real-time multiple-aspect representation of the individual products 201, and which are passing through the inspection station 33, with the controller 183, by utilizing the respective electromagnetic radiation detection device signals 187, and which are generated by the electromagnetic radiation detection devices 11, 20 and 30, respectively. The multiple-aspect representation has a plurality of features formed from the external and internal characteristics detected by the respective electromagnetic radiation detection devices 11, 20 and 30, respectively. The method includes still another step of sorting the individual products 201 based, at least in part, upon the multiple aspect representation formed by the controller, in real-time, as the individual products pass through the inspection station 33.

It should be understood that the multitude of external and internal characteristics and features of the individual products 201, in the product stream 202 are selected from the group comprising, but not limited to, color; light polarization; fluorescence; surface texture; and translucence to name but a few. It should be understood that the step of moving the stream of products 201 through an inspection station 33 further comprises releasing the stream of products, in one form of the invention, for unsupported downwardly directed, gravity influenced, movement through the inspection station 33, and positioning the plurality of electromagnetic radiation detection devices on opposite sides 51, and 52, of the unsupported stream of products 202. It is possible to also use the invention 10 to inspect products on a continuously moving conveyor belt 200, or on a downwardly declining chute (not shown). In the methodology as described above, the step of providing a plurality of electromagnetic radiation detection and emitting devices 11, 20, 30 and 40, respectively, in the inspection station 33, further comprises actuating the respective electromagnetic radiation detection devices, in real-time, so as to enhance the operation of the respective electromagnetic radiation detection and emitting devices, which are actuated. Still further, the step of providing a plurality of electromagnetic radiation detection and emitting devices 11, 20, 30 and 40, respectively, in the inspection station 33, further comprises selectively combining the respective electromagnetic radiation detection device signals 187 of the individual electromagnetic radiation detection devices to provide an increased contrast in the external and internal characteristics and features identified on/in the individual products 201, and which are passing through the inspection station 33. It should be understood that the step of generating a electromagnetic radiation detection device signal 187 by the plurality of electromagnetic radiation detection devices in the inspection station further includes identifying a gradient of the respective external and internal characteristics and features which are possessed by the individual products 201, which are passing through the inspection station 33.

In the methodology as described, above, the step of providing a plurality of electromagnetic radiation detection devices further comprises providing a plurality of selectively energizable electromagnetic radiation emitter illuminators 30, which emit, when energized, electromagnetic radiation 31, which is directed towards, and reflected from, refracted by, transmitted by or absorbed by individual products 201, and which are passing through the inspection station 33. The methodology further includes a step of providing a plurality of selectively operable electromagnetic radiation detector devices or image capturing devices 11, 20 and which are oriented so as to receive the reflected, refracted, transmitted electromagnetic radiation 31 from the individual products 201, and which are passing through the inspection station 33. The present method also includes another step of controllably coupling the controller 183 to each of the selectively energizable electromagnetic radiation emitter illuminators 30, and the selectively operable electromagnetic radiation detector image capturing devices 11, 20. In the arrangement as provided, and as discussed above, the selectively operable electromagnetic radiation detector image capturing devices are selected from the group comprising, but not limited to, laser scanners; line scanners; and the electromagnetic radiation detector image capturing devices which are oriented in different, perspectives, and orientations relative to the inspection station 33. The respective electromagnetic radiation detector image capturing devices are oriented so as to provide device signals 187 to the controller 183, and which would permit the controller 183 to generate a multiple aspect representation of the individual products 201 passing through the inspection station 33, and which have increased individual feature discrimination.

As should be understood, the selectively energizable electromagnetic radiation emitter illuminators 30 emit electromagnetic radiation, which is selected from the group comprising visible; invisible; collimated; non-collimated; focused; non-focused; pulsed; non-pulsed; phase-synchronized; non-phase-synchronized; polarized; and non-polarized electromagnetic radiation and to further the emitted electromagnetic radiation can be of various wavelengths so as to interact with various external and internal characteristics and features of the individual objects.

The method as described and discussed further includes a step of providing and electrically coupling an image preprocessor 184 with a controller 183. Before the step of delivering the device signals 187, which are generated by the respective electromagnetic radiation detection and emitting devices 11, 20, 30 and 40 to the controller 183, the methodology includes a step of delivering the electromagnetic radiation detection device signals 187 to the image preprocessor 184. Further, the step of delivering the device signal 187 to the image preprocessor further comprises, combining and correlating phase-specific and synchronized electromagnetic radiation detection device signals 187, by way of a sub-pixel digital alignment in a scaling and a correction of generated electromagnetic radiation detection device signals 187, which are received from the respective electromagnetic radiation detection and emitting devices 11, 20, 30 and 40, respectively.

The method of sorting, of the present invention, includes, in one possible form, a step of providing a source of products 201 to be sorted, and secondly, providing a conveyor 200 for moving the source of products 202 along the path of travel, and then releasing the products 201 to be sorted into a product stream 202 for unsupported gravity influenced movement through a downstream inspection station 33. In this particular form of the invention, the methodology includes another step of providing a first, selectively energizable electromagnetic radiation emitter illuminator 30, which is positioned elevationally above, or to the side of the product stream 202, and which, when energized, generates electromagnetic radiation waves 31 directed toward the product stream 202 which is moving through the inspection station 33. The methodology includes another step of providing a first, selectively operable electromagnetic radiation detector image capturing device 11, and which is operably associated with the first electromagnetic radiation emitter illuminator 30, and which is further positioned elevationally above, or to the side of the product stream 202, and which, when actuated, captures images of the illuminated product stream 202, moving through the inspection station 33. The method, as described herein, includes another step of providing a second selectively energizable electromagnetic radiation emitter illuminator 30, which is positioned elevationally below, or to the side of the product stream 202, and which, when energized, emits a narrow beam of electromagnetic radiation (light) 31, which is scanned along a path of travel, and across the product stream 202, which is moving through the inspection station 33. The method includes yet another step of providing a second, selectively operable electromagnetic radiation detection image capturing device 20, which is operably associated with the second electromagnetic radiation emitter illuminator 30, and which is further positioned elevationally above, or to the side of the product stream, and which, when actuated, captures images of the product stream 202, and which is illuminated by the narrow beam of light 31, and which is emitted by the second selectively energizable electromagnetic radiation emitter illuminator 30. The methodology includes another step of providing a third, selectively energizable electromagnetic radiation emitter illuminator 30, which is positioned elevationally below, or to the side of the product stream 202, and which, when energized, generates electromagnetic radiation waves 31 directed toward the product stream 202, and which is moving through the inspection station 33. In the methodology as described, the method includes another step of providing a third, selectively operable electromagnetic radiation detection image capturing device 11, and which is operably associated with the second electromagnetic radiation emitter illuminator 30, and which is further positioned elevationally below, or to the side of the product stream 202, and which further, when actuated, captures images of the illuminated product stream 202, moving through the inspection of station 33; and generating with the first, second and third electromagnetic radiation detection image capturing devices 11, an image signal 187, formed of the images generated by the first, second and third electromagnetic radiation detection imaging capturing devices. The methodology includes another step of providing a controller 183, and electrically coupling the controller 183 in controlling relation relative to each of the first, second and third electromagnetic radiation emitter illuminators 30, and electromagnetic radiation detection image capturing devices 11, respectively, and wherein the controller 183 is operable to individually and sequentially energize, and then render operable the respective first, second and third electromagnetic radiation emitter illuminators 30, and associated electromagnetic radiation detection image capturing devices 11 in a predetermined pattern, so that only one electromagnetic radiation emitter illuminator 30, and the associated electromagnetic radiation detection image capturing device 11, is energized or rendered operable during a given time period. The controller 183 further receives the respective image signals 187, which are generated by each of the first, second and third electromagnetic radiation detection image capturing devices 11, and which depicts the product stream 202 passing through the inspection station 33, in real-time. The controller 183 analyzes the respective image signals 187 of the first, second and third electromagnetic radiation detection image capturing devices 11, and identifies any unacceptable products 201 which are moving along in the product stream 202. The controller 183 generates a product ejection signal 204, which is supplied to an ejection station 203 (FIG. 9), and which is downstream of the inspection station 33.

In the method as described in the paragraph immediately above, the methodology includes another step of aligning the respective first and third electromagnetic radiation emitter illuminators 30, and associated electromagnetic radiation detection image capturing devices 11, with each other, and locating the first and third electromagnetic radiation emitter illuminators 30 on opposite sides 51, and 52 of the product stream 202. In the methodology of the present invention, the predetermined pattern of energizing the respective electromagnetic radiation emitter illuminators 30, and forming an image signal 187, with the associated electromagnetic radiation detection image capturing devices 11, further comprises the steps of first rendering operable the first electromagnetic radiation emitter illuminator 30, and associated electromagnetic radiation detection image capturing device 11 for a first pre-determined period of time; second rendering operable the second electromagnetic radiation emitter illuminator, and associated electromagnetic radiation detection image capturing device for a second predetermined period of time, and third rendering operable the third electromagnetic radiation emitter illuminator 30 and associated electromagnetic radiation detection image capturing device 11 for a third pre-determined period of time. In this arrangement, the first, second and third predetermined time periods are sequential in time. In the arrangement as provided, the step of energizing the respective electromagnetic radiation emitter illuminators 30 in a pre-determined pattern and electromagnetic radiation detection image capturing devices takes place in a time interval of about 50 microseconds to about 500 microseconds. As should be understood, the first predetermined time period is about 25 microseconds to about 250 microseconds; the second predetermined time period is about 25 microseconds to about 150 microseconds, and the third predetermined time period is about 25 microseconds to about 250 microseconds. In the methodology as described, the first and third electromagnetic radiation emitter illuminators comprise pulsed light emitting diodes; and the second electromagnetic radiation emitter illuminator comprises a laser scanner. Still further, it should be understood that the respective electromagnetic radiation emitter illuminators, when energized, emit electromagnetic radiation which lies in a range of about 400 nanometers to about 1,600 nanometers. It should be understood that the step of providing the conveyor 200 for moving the product 201 along a path of travel comprises providing a continuous belt conveyor, having an upper and a lower flight, and wherein the upper flight has a first intake end, and a second exhaust end, and positioning the first intake end elevationally above the second exhaust end. In the methodology of the prevent invention, the step of transporting the product with a conveyor 200 takes place at a predetermined speed of about 3 meters per second to about 5 meters per second. In one form of the invention, the product stream 202 moves along a predetermined trajectory, which is influenced, at least in part, by gravity, and which further acts upon the unsupported product stream 202. In at least one form of the present invention, the product ejection station 203 is positioned about 50 millimeters to about 150 millimeters downstream of the inspection station 33. As should be understood, the predetermined sequential time periods that are mentioned above, do not typically overlap.

The present invention discloses a method for sorting a product 10 which includes a first step of providing a source of a product 201 to be sorted; and a second step of transporting the source of the product along a predetermined path of travel, and releasing the source of product into a product stream 202 which moves in an unsupported gravity influenced free-fall trajectory along at least a portion of its path of travel. The method includes another step of providing an inspection station 33 which is located along the trajectory of the product stream 202; and a step of providing a first selectively energizable electromagnetic radiation emitter illuminator 30, and locating the first electromagnetic radiation emitter illuminator 30 to a first side of the product stream 202, and in the inspection station 33. The methodology of the present invention includes another step of providing a first, selectively operable electromagnetic radiation detection image capturing device 11, and locating the first electromagnetic radiation detection image capturing device 11 to the first side of the product stream 202. The present methodology includes another step of energizing the first electromagnetic radiation emitter illuminator 30, and rendering the first electromagnetic radiation detection image capturing device 11 operable, substantially simultaneously, for a first predetermined time period, so as to illuminate/irradiate the product stream 202, moving through the inspection station 33, and subsequently generate an image signal 187, with the first electromagnetic radiation detection image capturing device 11 of the illuminated/irradiated product stream 202. The present methodology 10 includes another step of providing a second, selectively energizable electromagnetic radiation emitter illuminator 30, and locating the second electromagnetic radiation emitter illuminator on a first side of the product stream 202, and in spaced relation relative to the first electromagnetic radiation emitter illuminator 30. The method includes another step of providing a second, selectively operable electromagnetic radiation detection image capturing device 11, and locating the second electromagnetic radiation detection image capturing device 11 on the first side of the product stream 202. The method includes another step of energizing the second electromagnetic radiation emitter illuminator 30 so as to generate a narrow beam of electromagnetic radiation or light 31, which is scanned across a path of travel which is transverse to the product stream 202, and which further is moving through the inspection station 33. The method, as described further, includes a step of rendering the second electromagnetic radiation detection image capturing device operable substantially simultaneously, for a second predetermined time period, and which is subsequent to the first predetermined time period. The second electromagnetic radiation emitter illuminator 30 illuminates/irradiates, with a narrow beam of electromagnetic radiation (light), the product stream 202, which is moving through the inspection station 33; and the second electromagnetic radiation detection image capturing device 20 subsequently generates an image signal 187 of the illuminated/irradiated product stream 202. The method includes another step of providing a third, selectively energizable electromagnetic radiation emitter illuminator 30, which is positioned to a second side of the product stream 202, and which, when energized, illuminates/irradiates the product stream 202 moving through the inspection station 33. The method includes still another step of providing a third, selectively operable electromagnetic radiation detection image capturing device 11, and locating the third electromagnetic radiation detection image capturing device 11 to the second side of the product stream 202. In the methodology as described, another step includes energizing the third electromagnetic radiation emitter illuminator 30, and rendering the third electromagnetic radiation detection image capturing device 11 substantially simultaneously operable for a third predetermined time period, so as to illuminate/irradiate the product stream 202 moving through the inspection station 33, while substantially simultaneously forming an image signal 187 with a third electromagnetic radiation detection image capturing device 11 of the illuminated product stream 202. In this arrangement, the third pre-determined time period is subsequent to the first and second predetermined time periods. The present methodology 10 includes another step of providing a fourth, selectively energizable electromagnetic radiation emitter illuminator 30, and locating the fourth electromagnetic radiation emitter illuminator to the second side of the product stream 202. The method includes another step of providing a fourth, selectively operable electromagnetic radiation detection image capturing device 11, and locating the fourth electromagnetic radiation detection image capturing device 11 on the second side of the product stream 202. The method includes another step of energizing the fourth electromagnetic radiation emitter illuminator 30 so as to generate a narrow beam of electromagnetic radiation or light 31, which is scanned across a path of travel which is transverse to the product stream 202, and which further is moving through the inspection station 33. The method, as described further, includes a step of rendering the fourth electromagnetic radiation detection image capturing device operable substantially simultaneously, for a fourth predetermined time period. The fourth electromagnetic radiation emitter illuminator 30 illuminates/irradiates, with a narrow beam of electromagnetic radiation (light), the product stream 202, which is moving through the inspection station 33; and the fourth electromagnetic radiation detection image capturing device 20 subsequently generates an image signal 187 of the illuminated/irradiated product stream 202. The method as described includes another step of providing a controller 183, and coupling the controller 183 in controlling relation relative to each of the first, second and third electromagnetic radiation detection image capturing devices 11, 20 and electromagnetic radiation emitter illuminators 30, respectively. The methodology includes another step of providing and electrically coupling an image preprocessor 184, with the controller 183, and supplying the image signals 187 which are formed by the respective first, second and third electromagnetic radiation detection image capturing devices 11, 20, to the image preprocessor 184. The methodology includes another step of processing the signal images 187, which are received by the image preprocessor 184, and supplying the image signals to the controller 183, so as to subsequently identify a defective product or a product having a predetermined undesirable characteristics/feature which may be external or internal, in the product stream 202, and which is passing through the inspection station 33. The controller 183 generates a product ejection signal when the defective product and/or product having a given characteristic/feature, is identified. The method includes another step of providing a product ejector 203, which is located downstream of the inspection station 33, and along the trajectory or path of travel of the product stream 202, and wherein the controller 183 supplies the product ejection signal 204 to the product ejector 203 to effect the removal of the identified defective product or product having a predetermined feature from the product stream.

The present invention 10 can be further described according to the following methodology. A method for sorting products 10 is described, and which includes the steps of providing a nominally continuous stream of individual products 201 in a flow of bulk particulate, and in which individual products 201 have multiple distinguishing features and characteristics, and where some of these features may be hidden or internal so as to not be easily discerned visually, in real-time. The methodology includes another step of distributing the stream of products 202, in a mono-layer of bulk particulate, and conveying or directing the products 201 through one or more automated inspection stations 33, and one or more automated ejection stations 203. The methodology includes another step of providing a plurality of electromagnetic radiation emitter illumination 30, and electromagnetic radiation detection devices 11 and 20, respectively, in the inspection station 33, and wherein the electromagnetic radiation emitter illumination and electromagnetic radiation detection devices use multiple modes of non-contact, non-destructive interrogation to identify distinguishing features and characteristics of the products 201, and wherein some of the multiple modes of non-contact, non-destructive product interrogation, if operated continuously, simultaneously and/or coincidently, destructively interfere with at least some of the interrogation result signals 187, and which are generated for the respective products 201, and which are passing through the inspection station 33. The methodology includes another step of providing a configurable, programmable, multi-phased, synchronizing interrogation signal acquisition controller 183, and an integrated interrogation signal data pre-processor 184, which is operably coupled to the electromagnetic radiation emitter illumination and electromagnetic radiation detection devices 30, 20 and 11, respectively, to selectively activate the individual electromagnetic radiation emitter illuminators, and electromagnetic radiation detectors in a programmable, pre-determined order specific to the individual products 201 being inspected to avoid any destructive, simultaneous, interrogation signal interference, and preserve spatially correlated and pixilated real-time interrogation signal image data 187, from each actuated detector 11 and 20, respectively, to the controller 183, as the products 201 pass through the inspection station 33. The methodology includes another step of providing sub-pixel level correction of spatially correlated, pixilated interrogation image data 187, from each actuated electromagnetic radiation detector 11 and 20, respectively, to form real-time, continuous, multi-modal, multi-dimensional, digital images representing the product flow 202, and wherein the multiple dimensions of digital data 187 indicate distinguishing features and characteristics of the individual products 201. The method includes another step of providing a configurable, programmable, real-time, multi-dimension interrogation signal data processor 182, which is operably coupled to the controller 183, and pre-processor 184, to identify products 201, and product features/characteristics possessed by the individual products from contrast gradients and predetermined ranges, and patterns of values specific to the individual products 201, from the preprocessed continuous interrogation data 187. The method 10 includes another step of providing one or more spatially and temporally targeted ejection devices 203, which are operably coupled to the controller 183, and preprocessor 184, to selectively re-direct selected objects or products 201 within the stream of products 202, as they individually pass through the ejection station 203.

Referring now to FIG. 1E, the first embodiment of the invention 10 is depicted, and is illustrated in one form. While simple in its overall arrangement, this first embodiment supports scan rates between the electromagnetic radiation detection device, shown as a camera 11, and the electromagnetic radiation detection device, shown as a laser scanner 20, of 2:1, and wherein the electromagnetic radiation detection device camera 11 can run twice the scan rate of the electromagnetic radiation detection device laser scanner 20. This is a significant feature because electromagnetic radiation detection device laser scanners are scan-rate limited by inertial forces due to the size and mass of the associated polygonal mirror used to direct a flying scan spot formed of electromagnetic radiation, to the inspection station 33. On the other hand, the camera 11 has no moving parts, and are scan-rate limited solely by the speed of the electronics and the amount of exposure that can be generated per unit of time that they are energized or actuated.

Referring now to FIG. 2, a second embodiment of the invention is shown, and which adds a second, opposite side electromagnetic radiation detection camera 55, which uses the time slot allotted to the first electromagnetic radiation detection camera's second exposure. This arrangement as seen in FIG. 2, is limited to 1:1 scan rates.

Referring now to FIG. 3, the third embodiment of the invention adds a second electromagnetic radiation detection laser scanner 20, which is phase-delayed from the first electromagnetic radiation detection scanner, to avoid having their respective scanned spots formed of electromagnetic radiation from being in the same place at the same time. As should be understood, fully coincident electromagnetic radiation detection laser scanner spots are one form of destructive interference, which the present invention avoids. This form of the invention is limited to 1:1 scan rates.

Referring now to FIG. 4, a fourth embodiment of the invention is shown and which divides the time slot allotted for each electromagnetic radiation detection camera 111a and 112a, respectively, when compared to the previous two embodiments, into two time slots, so that both cameras can run at twice the scan rate of the associated electromagnetic radiation detection laser scanner 20. The associated detector hardware configuration is the same as the second form of the invention, but control and exposure timing are different, and can be selectively changed by way of software commands such that a user (not shown) can select sorting and actuation patterns that use one mode, or the other, as appropriate for a particular sorting application.

Referring now to FIG. 5, a fifth form of the invention is illustrated and wherein a second electromagnetic radiation detection laser scanner 132b is provided, and which includes the scanning timing as seen in the fourth form of the invention. As noted above, the associated detector hardware configuration is the same as the third form of the invention, but control and exposure timing are different, and can be changed such that a user could select sorting steps that use only one mode or the other, as appropriate, for a particular sorting application.

Referring now to FIG. 6, the sixth form of the invention introduces a dual electromagnetic radiation detection camera arrangement 151 and 152, respectively, and wherein the electromagnetic radiation detection cameras view active backgrounds that are also foreground illumination for the opposite side electromagnetic radiation detection camera. Each electromagnetic radiation detection camera acquires both reflective and transmitted images which create another form of the multi-modal, multi-dimensional image. In this embodiment, each electromagnetic radiation detection camera scans at twice the overall system scan rate, but image data 187 is all at the overall system scan rate, since half of each of the electromagnetic radiation detection camera's exposure is for a different imaging mode prior to pixel data fusion, which then produces higher dimensional, multi-modal images at the system scan rate, which is provided.

Referring now to FIG. 7, this form of the invention adds a dual-mode reflection/transmission electromagnetic radiation detection camera operation embodiment of the sixth form of the invention with an electromagnetic radiation detection laser scanner 161B which is similar to the second and fourth embodiments. A difference in this arrangement is that either selectively active backgrounds are used in a detector arrangement as shown in FIG. 2 or 4, or electromagnetic radiation detection cameras are aimed at opposite side electromagnetic radiation emitter illuminators, as seen in FIG. 7. Using the detector arrangement, as shown in the second form of the invention, provides more flexibility but requires more hardware.

Referring now to FIG. 8, this form of the invention adds a second electromagnetic radiation detection laser scanner 172b to that seen in the seventh form of the invention, and further employs the time-phased approach as seen in the third and fifth forms of the invention. As should be understood, the present invention can be scaled to increase the number of electromagnetic radiation detection detectors and electromagnetic radiation emitters/illuminators.

The instant invention provides a method of sorting comprising providing a source of a product to be sorted, the product comprised of a plurality of individual items each having a multitude of external and internal characteristics that are perceptible, and wherein the multitude of external and internal characteristics that are perceptible are selected from a group including color; light polarization; light fluorescence; light reflectance; light scatter; light transmittance; surface texture; translucence; density; composition; structure and constituents, and wherein the multitude of external and internal characteristics that are perceptible can be detected and identified at least in part, from electromagnetic radiation which is spectrally reflected, refracted, fluoresced absorbed or transmitted by the multitude of external and internal perceptible characteristics of each of the plurality of individual items; conveying the plurality of individual items along a path of travel, and then releasing the plurality of individual items into a product stream for unsupported movement through a downstream inspection station for selective irradiation and contemporaneous collection of electromagnetic radiation which is either transmitted, reflected, refracted, fluoresced, emitted and/or scattered from each of the plurality of individual items; selectively energizing a first electromagnetic radiation emitter which is positioned on a first side of the product stream, and which, when energized, emits electromagnetic radiation at a first side of each of the plurality of individual items traveling in the unsupported product stream which is moving through the inspection station; selectively actuating a first electromagnetic radiation capturing device which is operably associated with the first electromagnetic radiation emitter, and which is further positioned on the first side of the unsupported product stream, and which, when actuated, captures electromagnetic radiation which is transmitted, reflected, refracted, fluoresced, emitted or scattered from each of the plurality of individual items and which are subjected to the electromagnetic radiation which was emitted by the energized first electromagnetic radiation emitter, and wherein the selectively actuated first electromagnetic radiation capturing device further generates a first interrogation signal; selectively energizing a second electromagnetic radiation emitter which is positioned on the first side of the unsupported product stream, and which, when energized, emits a narrow beam of electromagnetic radiation which is scanned along a path of travel, and across the unsupported product stream moving through the inspection station; selectively actuating a second electromagnetic radiation capturing device which is operably associated with the second electromagnetic radiation emitter, and which is further positioned on the first side of the product stream, and which, when actuated, captures electromagnetic radiation which is transmitted, reflected, refracted, fluoresced, emitted or scattered from each of the plurality of individual items moving through the inspection station, and which are subjected to the narrow beam of electromagnetic radiation emitted by the selectively energized second electromagnetic radiation emitter, and wherein the selectively actuated second electromagnetic radiation capturing device further generates a second interrogation signal; selectively energizing a third electromagnetic radiation emitter which is positioned on a second side of the unsupported product stream, and which, when energized, emits electromagnetic radiation which is directed at a second side of each of the plurality of individual items traveling in the unsupported product stream which is moving through the inspection station; selectively actuating a third electromagnetic radiation capturing device which is operably associated with the third electromagnetic radiation emitter, and which is further positioned on the second side of the product stream, and which, when actuated, captures electromagnetic radiation which is transmitted, reflected, refracted, fluoresced, emitted or scattered from each of the plurality of individual items moving through the inspection station, and which are subjected to the electromagnetic radiation emitted by the selectively energized third electromagnetic radiation emitter, and wherein the selectively actuated third electromagnetic radiation capturing device further generates a third interrogation signal; selectively energizing a fourth electromagnetic radiation emitter which is positioned on the second side of the unsupported product stream, and which, when energized, emits a narrow beam of electromagnetic radiation which is scanned along a path of travel, and across the unsupported product stream moving through the inspection station; selectively actuating a fourth electromagnetic radiation capturing device which is operably associated with the fourth electromagnetic radiation emitter, and which is further positioned on the second side of the product stream, and which, when actuated, captures electromagnetic radiation which is transmitted, reflected, refracted, fluoresced, emitted or scattered from each of the plurality of individual items moving through the inspection station, and which are subjected to electromagnetic radiation by the narrow beam of electromagnetic radiation emitted by the selectively energized fourth electromagnetic radiation emitter, and wherein the fourth selectively actuated electromagnetic radiation capturing device further generates a fourth interrogation signal; controllably coupling a controller with the first, second, third, and fourth selectively energizable electromagnetic radiation emitters, and each of the selectively actuated electromagnetic radiation capturing devices, respectively, and wherein the controller selectively and individually energizes the respective first, second, third, and fourth electromagnetic radiation emitters, and selectively and individually actuates each of the electromagnetic radiation capturing devices, in a predetermined sequence, so that only a predetermined electromagnetic radiation emitter and associated electromagnetic radiation capturing device or a cooperating combination of electromagnetic radiation emitters, and associated electromagnetic radiation capturing devices are selectively actuated or rendered operable, during a predetermined time period so as to substantially isolate the interrogation signals derived from each of the selectively actuated electromagnetic radiation capturing devices and to substantially impede spectral overlap, so as to prevent a destructive interference from developing between the respective selectively energized electromagnetic radiation emitters, and selectively actuated electromagnetic radiation capturing devices, and wherein the controller further receives the respective interrogation signals generated by the respective first, second, third, and fourth selectively actuated electromagnetic radiation capturing devices; analyzing with the controller, the respective interrogation signals received from the respective first, second, third, and fourth electromagnetic radiation capturing devices and detecting the multitude of external and internal characteristics of each of the plurality of individual items that are perceptible, and identifying individual items in the unsupported product stream that are acceptable and unacceptable, and wherein the controller generates, a product ejection signal when an unacceptable item is identified; and providing a product ejector downstream of the inspection station, and which receives the product ejection signal, and which ejects any of the plurality of individual items moving along the unsupported path of travel in the product stream that has been identified by the controller as unacceptable.

The instant method for sorting further comprises the step of aligning the respective first and second selectively energizable electromagnetic radiation emitters, and associated selectively actuated electromagnetic radiation capturing devices with each other to focus on a single focal plane, and locating the third and fourth selectively energizable electromagnetic radiation emitters, and associated selectively actuated electromagnetic radiation capturing devices, on the opposite side of the unsupported product stream and orienting the third and fourth selectively energizable electromagnetic radiation emitters and associated selectively actuated electromagnetic radiation capturing devices to focus on the single focal plane.

The instant method for sorting further comprises the step of aligning the respective selectively energizable second and fourth electromagnetic radiation emitters and associated selectively actuated electromagnetic radiation capturing devices with each other to focus on a single focal plane, and selectively energizing the respective second and fourth electromagnetic radiation emitters, and selectively actuating the associated electromagnetic radiation capturing devices, in a phase delayed operation on opposite sides of the product stream such that each selectively energizable electromagnetic radiation emitter does not destructively interfere with another selectively actuated electromagnetic radiation capturing device.

The instant method for sorting further comprises the step of determining a predetermined pattern of energizing the respective selectively energizable first, second, third and fourth electromagnetic radiation emitters, and forming the interrogation signals with the associated selectively actuated electromagnetic radiation capturing devices further comprises first, energizing the first electromagnetic radiation emitter, and actuating the associated electromagnetic radiation capturing device for a first predetermined period of time; second, energizing the second electromagnetic radiation emitter and actuating the associated electromagnetic radiation capturing device for a second, predetermined time period; third, energizing the third electromagnetic radiation emitter, and actuating the associated electromagnetic radiation capturing device for a third, predetermined time period; and fourth, energizing the fourth electromagnetic radiation emitter and actuating the associated electromagnetic radiation capturing device for a fourth, predetermined time period that is phase delayed from, and partially overlapping with the second predetermined time period, and wherein the first, second and third predetermined time periods are sequential, in time, and the fourth predetermined time period partially overlaps, and extends from the second predetermined time period.

The instant method for sorting further comprises the step of selectively energizing the respective electromagnetic radiation emitters in a predetermined pattern, and selectively actuating the electromagnetic radiation capturing devices in the predetermined pattern takes place in a time interval of about 50 microseconds to about 500 microseconds.

The instant method for sorting further comprises the step wherein the first predetermined time period is about 25 microseconds to about 250 microseconds; and the second predetermined time period is about 75 microseconds to about 150 microseconds; and the third predetermined time period is about 25 microseconds to about 250 microseconds; and the fourth predetermined time period is about 75 microseconds to about 150 microseconds, and partially overlaps with the second predetermined time period and is further phase delayed by about 5 microseconds to about 25 microseconds and effectively extends from the second predetermined time period by about 5 microseconds to about 25 microseconds.

The instant method for sorting further comprises the step wherein the first and third selectively energizable electromagnetic radiation emitters comprise pulsed light emitting diodes; and the second and fourth selectively energizable electromagnetic radiation emitters comprise laser scanners.

The instant method for sorting further comprises the step wherein the respective selectively energizable electromagnetic radiation emitters, when energized, emit electromagnetic radiation which lies in a range of about 400 nanometers to about 1600 nanometers wavelength.

The instant method for sorting further comprises the step wherein the step of conveying the product along a path of travel comprises providing a continuous belt conveyor having an upper and lower flight; and wherein the upper flight has a first intake end, and a second exhaust end; and positioning the first, intake end elevationally, above, the second, exhaust end.

The instant method for sorting further comprises conveying the product with the conveyor at a predetermined speed of about 3 meters per second to about 5 meters per second.

The instant method for sorting further comprises the step wherein the product stream moves along a predetermined trajectory which is influenced, at least in part, by gravity which acts upon the unsupported product stream.

The instant method for sorting further comprises locating the product ejector about 50 millimeters to about 150 millimeters downstream of the inspection station.

The instant method for sorting further comprises the step wherein the predetermined sequential time periods do not substantially overlap.

The instant method for sorting further comprises the step wherein the multitude of external and internal characteristics of the plurality of individual items are humanly perceptible.

The instant method for sorting further comprises the step wherein the multitude of external and internal characteristics of the plurality of individual items are machine perceptible.

The instant method for sorting further comprises the step wherein the multitude of external and internal characteristics of the plurality of individual items are humanly invisible.

Therefore, it will be seen that the present invention provides a convenient means whereby the destructive interference that might result from the operation of multiple detectors and illuminators is substantially avoided, and simultaneously provides a means for collecting multiple levels of data, which can then be assembled, in real-time, to provide a means for providing intelligent sorting decisions in a manner not possible heretofore.

In compliance with the statute, the invention has been described in language more or less specific as to structural and methodical features. It is to be understood, however, that the invention is not limited to the specific features shown and described since the means herein disclosed comprise preferred forms of putting the invention into effect. The invention is, therefore, claimed in any of its forms or modifications within the proper scope of the appended claims appropriately interpreted in accordance with the Doctrine of Equivalence.

We claim:

1. A method for sorting an agricultural product comprising:
   providing a source of an agricultural product to be sorted, the agricultural product comprised of a plurality of individual items each individual item having a multitude of internal and below surface characteristics, and wherein the multitude of internal and below surface characteristics are not visually discernable but are machine perceptible and are selected from a group including; light polarization; light fluorescence; light reflectance; light scatter; light transmittance; surface texture; translucence; density; composition; structure and constituents, and wherein the multitude of internal and below surface characteristics that are machine perceptible can be detected and identified at least in part, from electromagnetic radiation which is spectrally reflected, refracted, fluoresced absorbed or transmitted by the multitude of internal and below surface characteristics of each of the plurality of individual items;
   conveying the plurality of individual items along a path of travel, and then releasing the plurality of individual items into a product stream for unsupported movement through a downstream inspection station for selective irradiation and contemporaneous collection of electromagnetic radiation which is either transmitted, reflected, refracted, fluoresced, emitted and/or scattered from each of the plurality of individual items;
   selectively energizing a first electromagnetic radiation emitter which is positioned on a first side of the product stream, and which, when energized, emits electromagnetic radiation at a first side of each of the plurality of individual items traveling in the unsupported product stream which is moving through the inspection station;
   selectively actuating a first electromagnetic radiation capturing device which is operably associated with the first electromagnetic radiation emitter, and which is further positioned on the first side of the unsupported product stream, and which, when actuated, captures substantially only electromagnetic radiation which is transmitted, reflected, refracted, fluoresced, emitted or scattered from each of the plurality of individual items and which are subjected to the electromagnetic radiation emitted by the energized first electromagnetic radiation emitter, and wherein the selectively actuated first electromagnetic radiation capturing device further generates a first interrogation signal;
   selectively energizing a second electromagnetic radiation emitter which is positioned on the first side of the unsupported product stream, and which, when energized, emits a narrow beam of electromagnetic radiation which is scanned along a path of travel, and across the unsupported product stream moving through the inspection station;
   selectively actuating a second electromagnetic radiation capturing device which is operably associated with the second electromagnetic radiation emitter, and which is further positioned on the first side of the product stream, and which, when actuated, captures substantially only electromagnetic radiation which is transmitted, reflected, refracted, fluoresced, emitted or scattered from each of the plurality of individual items moving through the inspection station, and which are subjected to the narrow beam of electromagnetic radiation emitted by the selectively energized second electromagnetic radiation emitter, and wherein the selectively actuated second electromagnetic radiation capturing device further generates a second interrogation signal;
   selectively energizing a third electromagnetic radiation emitter which is positioned on a second side of the unsupported product stream, and which, when energized, emits electromagnetic radiation which is directed at a second side of each of the plurality of individual items traveling in the unsupported product stream which is moving through the inspection station;
   selectively actuating a third electromagnetic radiation capturing device which is operably associated with the third electromagnetic radiation emitter, and which is further positioned on the second side of the product stream, and which, when actuated, captures substantially only electromagnetic radiation which is transmitted, reflected, refracted, fluoresced, emitted or scattered from each of the plurality of individual items moving through the inspection station, and subjected to the electromagnetic radiation emitted by the selectively energized third electromagnetic radiation emitter, and wherein the selectively actuated third electromagnetic radiation capturing device further generates a third interrogation signal;
   selectively energizing a fourth electromagnetic radiation emitter which is positioned on the second side of the unsupported product stream, and which, when energized, emits a narrow beam of electromagnetic radiation which is scanned along a path of travel, and across the unsupported product stream moving through the inspection station;
   selectively actuating a fourth electromagnetic radiation capturing device which is operably associated with the fourth electromagnetic radiation emitter, and which is further positioned on the second side of the product stream, and which, when actuated, captures substantially only electromagnetic radiation which is transmitted, reflected, refracted, fluoresced, emitted or scattered from each of the plurality of individual items moving through the inspection station, and which are subjected to electromagnetic radiation by the narrow beam of electromagnetic radiation emitted by the selectively energized fourth electromagnetic radiation emitter, and wherein the fourth selectively actuated electromagnetic radiation capturing device further generates a fourth interrogation signal;

controllably coupling a controller with the first, second, third, and fourth selectively energizable electromagnetic radiation emitters, and each of the selectively actuated electromagnetic radiation capturing devices, respectively, and wherein the controller selectively and individually energizes the respective first, second, third, and fourth electromagnetic radiation emitters, and selectively and individually actuates each of the electromagnetic radiation capturing devices, in a predetermined sequence, so that only a predetermined electromagnetic radiation emitter and associated electromagnetic radiation capturing device are selectively actuated or rendered operable, during a predetermined time period so as to substantially isolate the interrogation signals derived from each of the selectively actuated electromagnetic radiation capturing devices and to substantially impede spectral overlap, so as to prevent a destructive interference from developing between the respective selectively energized electromagnetic radiation emitters, and selectively actuated electromagnetic radiation capturing devices, and analyzing the respective interrogation signals received from the respective first, second, third, and fourth electromagnetic radiation capturing devices and detecting the multitude of internal and below surface characteristics of each of the plurality of individual items, and identifying individual items in the unsupported product stream that are acceptable and unacceptable, and wherein the controller generates, a product ejection signal when an unacceptable item is identified; and providing a product ejector downstream of the inspection station, and which receives the product ejection signal, and which ejects any of the plurality of individual items moving along the unsupported path of travel in the product stream that has been identified by the controller as unacceptable.

2. The method for sorting as claimed in claim 1, and further comprising the step:

aligning the respective first and second selectively energizable electromagnetic radiation emitters, and associated selectively actuated electromagnetic radiation capturing devices with each other to focus on a single focal plane, and locating the third and fourth selectively energizable electromagnetic radiation emitters, and associated selectively actuated electromagnetic radiation capturing devices, on the opposite side of the unsupported product stream and orienting the third and fourth selectively energizable electromagnetic radiation emitters and associated selectively actuated electromagnetic radiation capturing devices to focus on the single focal plane.

3. The method for sorting as claimed in claim 1, and further comprising the step:

aligning the respective selectively energizable second and fourth electromagnetic radiation emitters and associated selectively actuated electromagnetic radiation capturing devices with each other to focus on a single focal plane, and selectively energizing the respective second and fourth electromagnetic radiation emitters, and selectively actuating the associated electromagnetic radiation capturing devices, in a phase delayed operation on opposite sides of the product stream such that each selectively energizable electromagnetic radiation emitter does not destructively interfere with another selectively actuated electromagnetic radiation capturing device.

4. The method for sorting as claimed in claim 1, and wherein the predetermined pattern of energizing the respective selectively energizable first, second, third and fourth electromagnetic radiation emitters, and forming the interrogation signals with the associated selectively actuated electromagnetic radiation capturing devices further comprises first, energizing the first electromagnetic radiation emitter, and actuating the associated electromagnetic radiation capturing device for a first predetermined period of time; second, energizing the second electromagnetic radiation emitter and actuating the associated electromagnetic radiation capturing device for a second, predetermined time period; third, energizing the third electromagnetic radiation emitter, and actuating the associated electromagnetic radiation capturing device for a third, predetermined time period; and fourth, energizing the fourth electromagnetic radiation emitter and actuating the associated electromagnetic radiation capturing device for a fourth, predetermined time period that is phase delayed from, and partially overlapping with the second predetermined time period, and wherein the first, second and third predetermined time periods are sequential, in time, and the fourth predetermined time period partially overlaps, and extends from the second predetermined time period.

5. The method for sorting as claimed in claim 1, and wherein the step of selectively energizing the respective electromagnetic radiation emitters in a predetermined pattern, and selectively actuating the electromagnetic radiation capturing devices in the predetermined pattern takes place in a time interval of about 50 microseconds to about 500 microseconds.

6. The method for sorting as claimed in claim 4, and wherein the first predetermined time period is about 25 microseconds to about 250 microseconds; and the second predetermined time period is about 75 microseconds to about 150 microseconds; and the third predetermined time period is about 25 microseconds to about 250 microseconds; and the fourth predetermined time period is about 75 microseconds to about 150 microseconds, and partially overlaps with the second predetermined time period and is further phase delayed by about 5 microseconds to about 25 microseconds and effectively extends from the second predetermined time period by about 5 microseconds to about 25 microseconds.

7. The method for sorting as claimed in claim 1, and wherein the first and third selectively energizable electromagnetic radiation emitters comprise pulsed light emitting diodes; and the second and fourth selectively energizable electromagnetic radiation emitters comprise laser scanners.

8. The method for sorting as claimed in claim 1, and wherein the respective selectively energizable electromagnetic radiation emitters, when energized, emit electromagnetic radiation which lies in a range of about 400 nanometers to about 1600 nanometers wavelength.

9. The method for sorting as claimed in claim 1, and wherein the step of conveying the product along a path of travel comprises providing a continuous belt conveyor having an upper and lower flight; and wherein the upper flight has a first intake end, and a second exhaust end; and positioning the first, intake end elevationally, above, the second, exhaust end.

10. The method for sorting as claimed in claim 9, and further comprising conveying the product with the conveyor at a predetermined speed of about 3 meters per second to about 5 meters per second.

11. The method for sorting as claimed in claim 1, and wherein the product stream moves along a predetermined trajectory which is influenced, at least in part, by gravity which acts upon the unsupported product stream.

12. The method for sorting as claimed in claim 1, and further comprising locating the product ejector about 50 millimeters to about 150 millimeters downstream of the inspection station.

13. The method for sorting as claimed in claim 4, and wherein the predetermined sequential time periods do not substantially overlap.

14. The method for sorting as claimed in claim 1, and wherein the multitude of external and internal characteristics of the plurality of individual items are not humanly perceptible.

15. The method for sorting as claimed in claim 1, and wherein the multitude of external and internal characteristics of the plurality of individual items are machine perceptible.

16. The method for sorting as claimed in claim 1, and wherein the multitude of external and internal characteristics of the plurality of individual items are humanly invisible.

* * * * *

UNITED STATES PATENT AND TRADEMARK OFFICE
CERTIFICATE OF CORRECTION

PATENT NO. : 10,195,647 B2  
APPLICATION NO. : 15/708743  
DATED : February 5, 2019  
INVENTOR(S) : Dirk Adams et al.

Page 1 of 1

It is certified that error appears in the above-identified patent and that said Letters Patent is hereby corrected as shown below:

In the Specification

Column 1: Line 25: Delete the word "be" and insert the word --been--.

Column 3: Line 54: Insert a --,-- after the word --fluoresced--.

Column 20: Line 28: Delete the "," after the word --different--.

Column 27: Line 43: Insert a --,-- after the word --fluoresced--.

In the Claims

Column 31: Line 35: Delete the ";" after the word --including-- and insert a --:-- after the word --including--.

Column 31: Line 42: Insert a --,-- after the word --fluoresced--.

Signed and Sealed this  
Eighteenth Day of June, 2019

Andrei Iancu  
*Director of the United States Patent and Trademark Office*